US011932909B2

(12) United States Patent
Meijer et al.

(10) Patent No.: US 11,932,909 B2
(45) Date of Patent: Mar. 19, 2024

(54) METHYLATION CLASSIFIER FOR DETECTION OF HPV-INDUCED INVASIVE CANCERS, NONHPV-INDUCED GYNAECOLOGICAL AND ANOGENITAL CANCERS AND THEIR HIGH-GRADE PRECURSOR LESIONS

(71) Applicant: SELF-SCREEN B.V., Amsterdam (NL)

(72) Inventors: Christophorus Joannes Lambertus Maria Meijer, Leiden (NL); Renske Daniëla Maria Steenbergen, Amstelveen (NL); Petrus Josephus Ferdinandus Snijders, Amstelveen (NL); Daniëlle Anne Marie Heideman, Amsterdam (NL)

(73) Assignee: SELF-SCREEN B.V., Amsterdam (NL)

( * ) Notice: Subject to any disclaimer, the term of this patent is extended or adjusted under 35 U.S.C. 154(b) by 184 days.

(21) Appl. No.: 16/491,182

(22) PCT Filed: Mar. 9, 2018

(86) PCT No.: PCT/NL2018/050143
§ 371 (c)(1),
(2) Date: Sep. 5, 2019

(87) PCT Pub. No.: WO2018/164577
PCT Pub. Date: Sep. 13, 2018

(65) Prior Publication Data
US 2020/0032348 A1 Jan. 30, 2020

(30) Foreign Application Priority Data
Mar. 10, 2017 (EP) .................................... 17160346

(51) Int. Cl.
 *C12Q 1/68* (2018.01)
 *C07H 21/04* (2006.01)
 *C12Q 1/6886* (2018.01)

(52) U.S. Cl.
CPC ...... *C12Q 1/6886* (2013.01); *C12Q 2600/112* (2013.01); *C12Q 2600/154* (2013.01)

(58) Field of Classification Search
None
See application file for complete search history.

(56) References Cited

U.S. PATENT DOCUMENTS

2011/0300536 A1   12/2011   Li et al.

FOREIGN PATENT DOCUMENTS

| JP | 2012523822 A | 10/2012 |
|---|---|---|
| JP | 2015532108 A | 11/2015 |
| WO | 2013174432 A1 | 11/2013 |
| WO | 2014058321 A1 | 4/2014 |
| WO | 2016048138 A1 | 3/2016 |
| WO | 2016115354 A1 | 7/2016 |
| WO | 2017034407 A1 | 3/2017 |

OTHER PUBLICATIONS

Lechner et al. (Genome Medicine, vol. 5, No. 15, 2013). (Year: 2013).*
NEB catalog (1998/1999), pp. 121, 284. (Year: 1998).*
Farkas et al. "Genome-wide DNA methylation assay reveals novel candidate biomarker genes in cervical cancer." Epigenetics 8.11 (2013): 1213-1225. 14 pages.
No Author. "Infinium HumanMethylation450 BeadChip." Mar. 9, 2012, XP055401052. https://support.illumina.com/content/dam/illumina-marketing/documents/products/datasheets/datasheethumanmethylation450.pdf. Retrieved on Aug. 24, 2017. 4 pages.
Trimarchi et al. "Identification of endometrial cancer methylation features using combined methylation analysis methods." PloS One 12.3 (2017): e0173242. 17 pages.
International Search Report and Written Opinion in corresponding International Patent Application No. PCT/NL2018/050143 dated May 14, 2018. 19 pages.
Sichero et al., "Identification of Novel Cellular Transcription Factors that regulate early promoters of human papillomavirus types 18 and 16", The Journal of Infectious Diseases, 2012, 2016(6): 867-874.
Office Action in corresponding Eurasian Patent Application No. 201991883, dated Mar. 4, 2022.
Office Action and English translation for corresponding Japanese Application No. 2019-549400, dated Nov. 26, 2021. 17 pages.

* cited by examiner

*Primary Examiner* — Jeanine A Goldberg
(74) *Attorney, Agent, or Firm* — Leason Ellis LLP

(57) ABSTRACT

The invention relates to method for detecting HPV-induced high-grade precancerous lesions, HPV-induced invasive cancers and nonHPV-induced gynaecological and anogenital cancers, said method comprising detection of a methylation classifier consisting of the genes LHX8, ASCL1 and ST6GALNAC5 and their regulatory sequence in a cell whereby such hypermethylation indicates the presence of HPV-induced precursor lesions with invasive potential, HPV-induced invasive cancers and nonHPV-induced gynaecological and anogenital cancers. The invention further comprises the use of the methylation classifier consisting of genes LHX8, ASCL1 and ST6GALNAC5 and their regulatory sequence in such a method and a test kit for the detection of LHX8. ASCL1 and/or ST6GALNAC5 methylation.

16 Claims, 10 Drawing Sheets
Specification includes a Sequence Listing.

Figure 1: ASCL1 sequence (regulatory region and exon1) derived from Refseq NM_004316 9hg19). The coding sequence is in upper case and underlined is the CpG rich region. (SEQ ID NO: 22)

```
>hg19_refGene_NM_004316
ttctttatgatatccgctaagctggtccggaaataatctttatggggagg
gggtggcggtaggggcgatggtacaggggccagaggtcatcctagggg
gacgtccctgccatatacaccacctacaggacggctcacaaccactcct
cggtgtcgcttcccgcggccccacacacttgctcagttatggggagc
acatcctagttttagagctgaatgggacattagagaccatattctgtgg
ctgcagacgaggaagcgaaggctcagagaggatgccacttcgaggagcca
cagagcattgagaggacgccttgggactagaacccacgttttcacatagt
ccagcactttttttcactgttctggacggagtcctccccaaccatgtt
tctaaacttcaatcgtaatttgctccaattctagggtcaccgaggaacc
cgaagagaataacagtgaggagagagaaaacaggaaaagtcgagcccc
actccctcctcacctccacaccgttcctgtgccattttttctgcccaaac
ccttccctgcgctttgcttcaagttcttagtagaatccaagagagcttca
ccccaagtctttccacctatacacctcaattcctagagccatttgtccct
cctgtgacgcccccacccccttcctaaagccaccccggcagcagcccg
cccgagcgcgcgcctgtttattcagccgggagtccggcacgcgccagg
cgcacgcactgcaacaacaaaccagctgaatggagagtttgcaaggagc
gggagaaaggaacgggaggggggagaggagaggaggagggagtttag
ggagtgggtgggaggaagaggtaagaggaggggggagtggggctgca
gccgctcgctgcagcagcgggagtgggggcgaggcggggccagggctg
cgcgtgggctgggtgtccattgaaaaggcggacgcactccggcagccc
AGCACTCTCTCACTTCTGGCCAGGGAACGTGGAAGGCGCACCGACAGGGA
TCCGGCCAGGGAGGGCGAGTGAAAGAAGGAAATCAGAAAGGAAGGGAGTT
AACAAAATAATAAAAACAGCCTGAGCCACGGCTGGAGAGACCGAGACCCG
GCGCAAGAGAGCGCAGCCTTAGTAGGAGAGGAACGCGAGACGCGGCAGAG
CGCGTTCAGCACTGACTTTTGCTGCTGCTTCTGCTTTTTTTTTTCTTAGA
AACAAGAAGGCGCCAGCGGCAGCCTCACACGCGAGCGCCACGCGAGGCTC
CCGAAGCCAACCCGCGAAGGGAGGAGGGGAGGGAGGAGGAGGCGGCGTGC
AGGGAGGAGAAAAGCATTTTCACTTTTTTTGCTCCCACTCTAAGAAGTC
TCCCGGGGATTTTGTATATATTTTTAACTTCCGTCAGGGCTCCCGCTTC
ATATTCCTTTTCTTTCCCTCTCTGTTCCTGCACCCAAGTTCTCTCTGTG
TCCCCCTCGCGGGCCCCGCACCTCGCGTCCCGGATCGCTCTGATTCCGCG
ACTCCTTGGCCGCCGCTGCGCATGGAAAGCTCTGCCAAGATGGAGAGCGG
CGGCGCCGGCCAGCAGCCCCAGCCGCAGCCCCAGCAGCCCTTCCTGCCGC
CCGCAGCCTGTTTCTTTGCCACGGCCGCAGCCGCGGCGGCCGCAGCCGCC
GCAGCGGCAGCGCAGAGCGCGCAGCAGCAGCAGCAGCAGCAGCAGCAGCA
GCAGCAGGCGCCGCAGCTGAGACCGGCGGCCGACGGCCAGCCCTCAGGGG
GCGGTCACAAGTCAGCGCCCAAGCAAGTCAAGCGACAGCGCTCGTCTTCG
CCCGAACTGATGCGCTGCAAACGCCGGCTCAACTTCAGCGGCTTTGGCTA
CAGCCTGCCGCAGCAGCAGCCGGCCGCCGTGGCGCGCCGCAACGAGCGCG
AGCGCAACCGCGTCAAGTTGGTCAACCTGGGCTTTGCCACCCTTCGGGAG
CACGTCCCCAACGGCGCGGCCAACAAGAAGATGAGTAAGGTGGAGACACT
GCGCTCGGCGGTCGAGTACATCCGCGCGCTGCAGCAGCTGCTGGACGAGC
ATGACGCGGTGAGCGCCGCCTTCCAGGCAGGCGTCCTGTCGCCCACCATC
TCCCCAACTACTCCAACGACTTGAACTCCATGGCCGGCTCGCCGGTCTC
ATCCTACTCGTCGGACGAGGGCTCTTACGACCCGCTCAGCCCCGAGGAGC
AGGAGCTTCTCGACTTCACCAACTGGTTCTGAGGGGCTCGGCCTGGTCAG
GCCCTGGTGCGAATGGACTTTGGAAGCAG
```

Figure 2: LHX8 sequence (regulatory region and exon1) derived from Refseq NM_001001933 (hg19). The coding sequence is in upper case and underlined is the CpG rich region. (SEQ ID NO: 23)

```
>hg19_refGene_NM_001001933
acatgtagagaaggcgggttttcctgaaagaggcgaagcaatttctccag
gaaagactttccccacacgccccttcctttatattaggttccaccctc
tggaaaacaaaacttttttttttttcttttcctggagggactcaggaaaa
gctcagtgctcacttcactcagagctcagtgaagctgggaaaggaattt
aagaacggttcatcagaaagtggtcaggccacagcggcctctttggacga
agacacacttgtagcattatccttctcggcatcagcttttattagtggat
cggggcggggagggggagatcggcagacacggacagcctctgaccctc
tggagttggtatgtgataagcagccctagcagtgccatgtattggaagaa
cgatcagatgtttgtgtgtaaactagtagcaaaggacgtgccggagctgg
cagttcccctgagaaggtgagcgagccgacgcctggcagaccagctga
atcgcagtgtccttgaaactcgagttgtttgggctcctaaacaaggttca
gaaactacctgtaacggcctcatcttcagacctggcaattttttttttt
attacgtagtagcgttagtcagtaatcattgcactccctcccaaaagct
cacttaacctgagacatggagactgtaatttgggagatgaagcctcgagc
ctaaggcgctctcaggtccatgtgagtcgtgcttttgttctatttgctgt
ggtgatcgtggcggtccgggagagtgggtcgggaggactgggcggctgtc
gggtggaaccggagacctggctcgtttcgttcggctgccgcggacactt
gctgcctgaggcacacctccctctgcggggctccagaaaggcctccgg
gatccctgggcttgccgggagagccatttacctaaaatgccaaaagaaa
acgcagggcacaaaacgagtcacgcggtttgtctgagtagactggggaa
gctgacaagctctcacctcactcggggaggcaggacctgtgggtatttggt
gttttaagtttgaaatcatctgcagcctgtctgagggcctcagcaggacg
cgcgcggggcgccctgactatttctttgctccgaagccggttggggaca
ccaggcgaaagcggagctgttctgtttaaacgccctttgtgtgtgaggac
gcggcctcagtgcagctacgctgggtcccgcgtagggagcgcacccaga
aagggagggtctcggccgacggtccggaggccccaggttggtatcttg
cctggtgcttcagaggggagggagaaggggaggcgaacagtcagaaatgc
agaagtgcgagccgctcgagttcggggtaccacccgccccgagctaga
gttttggaaacgaaagcggtctaagcccagggacgctgcgttttcgttt
aagaacaaaactccagcaaatacttggaaacacttgagtaacgcgcgttg
tttctttaaaacattttgtcagaggttgggtgagttcttttaatggcaca
aattaaattcagctggatatttttccattattctaccggcttttgcgctg
gttaaaaataatcctttagtagctcaaatgttgacttactgagcaataag
tggcaatttacaccttaaagaaacgagtgtaaatcactcgccactctaat
tgctgtaagtttacgaaagagctgctggctcggtttaatctgaagcattt
tcattcaaattgtcatcggaacaaacaccaggcttcttaaatcccgctgt
aattagctttcaagtatcctattaaacctcttcacctttgggctatcct
attcaaaaagccccttttttaaaatatatatgtgtcttgctcttttaatt
gaggttattaaagaaatctagttcttctcccacccctcctcaatcctc
ttttcttctctgcactccacctcccactgcccgcaccccctttagccc
ggtgttccccgctccgctatgattgacgtctggaaagaagagctttgtg
agggatgattgttattaacttgttatcccggcgggggggcgggaacc
gacgtgccgggtgagcgccggagacccggagccggggagcgcgggacg
agctaccagcgctcgggtggcggccgccagcggcagcgaaggaggctgc
gcgccagccgccgcgggcgccgggctcaggcgccgtgacggctgcacg
cgctgcccgcactctgagggccttcattagctcgctccccgcgccgagg
ctggggcggcagcacgctcggaacttctgatctgtttctccatactttc
tcccctcctactccgcagTGTCAGGGGCTCATGTCAGAGGAGTGCGGGC
GGACTACAGCCCTGGCGGCCGGGAGGACTCGCAAAGGCGCCGGGGAAGAG
GGACTG
```

Figure 3: ST6GALNAC5 sequence (regulatory region, exon1, intron 1 and exon 2) derived from Refseq NM_030965 (hg19). The coding sequence is in upper case and underlined is the CpG rich region. (SEQ ID NO: 24)

```
>hg19_refGene_NM_030965
agatgttaagtaatacattaagacaactattttcactgagcaatttcaca
agaaatatgttttagctaaattagacatttaacaaatgccatttgtaat
tcaatgcagaggagacagcatccttaaaacaagctattgatgtgactttc
ccaacataaacaatacttatgttttttaattttaattgaagtcctgaa
tgtgaaactatcgccgtcagtgcagtagaccaacggaaagcaccaaatac
cttaggattatgaaataagccatatgcagttttatctagcagacagaa
attcttcatccaaattaggaagaatctacaggtcaagttaatcatgtagc
tgtgacgtgctgaatgttttaaaactttaagatcatttagatgaacact
aggaaactcagaggtcaggcagaaatgtaaattgtaatattcaatgaaaa
taataaatgaaataattgagatgaaatattatctaaagaatgcatgagaa
taactgaatctgataaagtaaaattaaaattaagagagaagagaaaataa
gaaagtgagcaattgaaaaacggaataataaataatttttaagaaaaat
aatttcatcatgtatttctctatgctacgtacataaacgcaaacgctata
aatagagttattgacatttggggaggttgatttgttttatcaacatcgca
aaacagaaaatttaggttcagattttcacatggctatcacgttcagaat
ccaatcaggttctccttctttactacttgatgacttctttaaagataaat
aagccgcggaccaagaagtgggtacactggctcggttaactctctctcc
ccagaaatttcactactgaaaagattattatttggggcggggaaggggga
tgtagaggtctttaggaccagcaggcggcggcaggcggcagttgtgtag
atcgctgagagactacgagggtccggttcagttttaattctgtctctaat
CTCTGCAACAGCCGCGCTTCCCGGGTCCCGCGGCTCCCGCGCGCGATCTG
CCGCGGCCGGCTGCTGGGCAAAAATCAGAGCCGCCTCCGCCCATTACCC
ATCATGGAAACCCTCCAGGAAAAAGTGGCCCCGGACGCGCGAGCCTGAGG
ATTCTGCACAAAGAGGTGCCCAAAATGAAGACCCTGATGgtgagtcagt
tgtggcaactccacggcaaagagggggatccccgggctcagggtccac
gggacgcaccgtggagactccgagacgcctaaccctgggccgcgaggtcg
cctgttacaaagggacaacttctacccgctccgcgttccctcccgattc
tccagctctgcctggctcggaatccagagccaggatgggaactcggggt
tgcctcgcctcctagatctccggcgagaggtccgagggggtggcggagag
ctgcaggagcgatggaggagtgggcagattgctcaagggatggggtgcc
caaaagcaacagcctgccaaaaactaagagggacggggagggggacctt
tgcagactttcttcgttttcttagatttcaaacttgcaaggatcgcaagg
```
<u>atccagggcccaggaaaggagggtgtgaaggactcaaaattccagcag</u>
<u>cttggctggggtggctgcgccagacgggcccttcccaaagtgcaaaccc</u>
<u>accctgtcctcggcccggcgcgctccctcctcagccggggcgtac</u>
<u>accacctgccctctaccgagagatctgggcggcggcggccgaaagcagcg</u>
<u>acgcgccggagcatcccttcgatacgctaggggacggtgctttctctg</u>
<u>tcccagttgcgtcggcggggctggggccaggccgcccaaatctcccc</u>
<u>cactagagtgaccaccgcacagttgtcccgctgggcgcgctcctccggt</u>
<u>gtctgcgctcagccgctctcctcttctctctccgcccgccgcagCGCC</u>
<u>ATGGTCTGGCAGTGTGTTTAGCGCTCACCACCATGTGCACCAGCTTGTTG</u>
CTAGTGTACAGCAGCCTCGGCGGCCAGAAGGAGCGGCCCCGCAGCAGCA
GCAGCAGCAGCAGCAACAGCAGCAGCAGGCGTCGGCCACCGGCAGCTCGC
AGCCGGCGGCGGAGAGCAGCACCCAGCAGCGCCCCGGGGTCCCCGCGGGA
CCGCGGCCACTGGACGGATACCTCGGAGTGGCGGACCAGAAG Figure 4
A. hrHPV-positive lavage self-samples
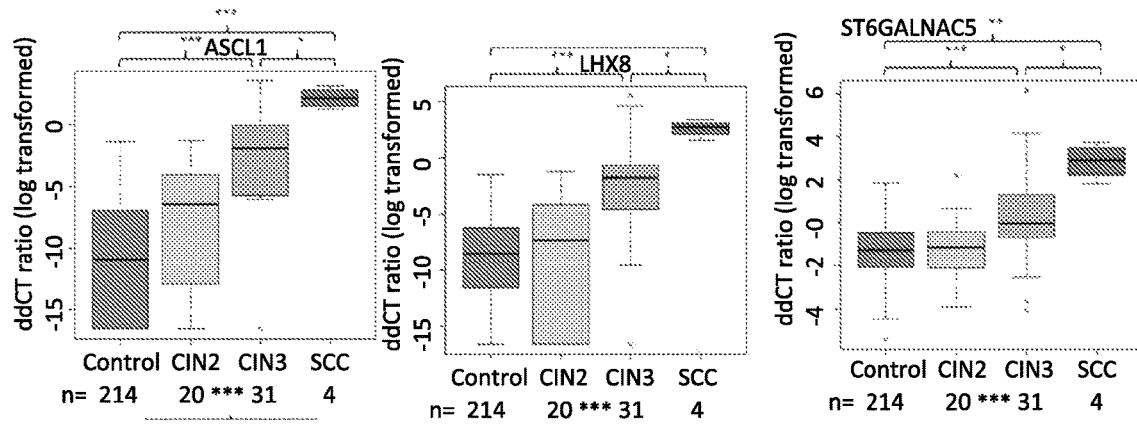
B. hrHPV-positive brush self-samples
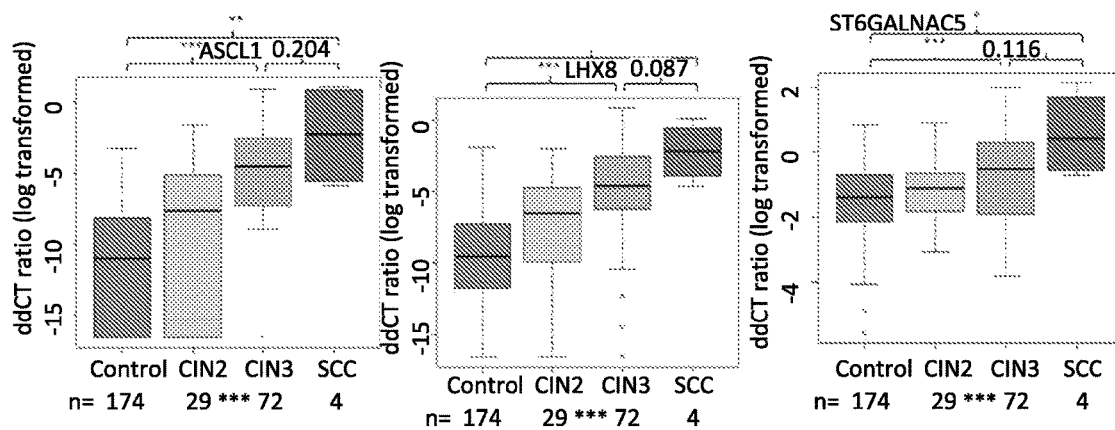
C.
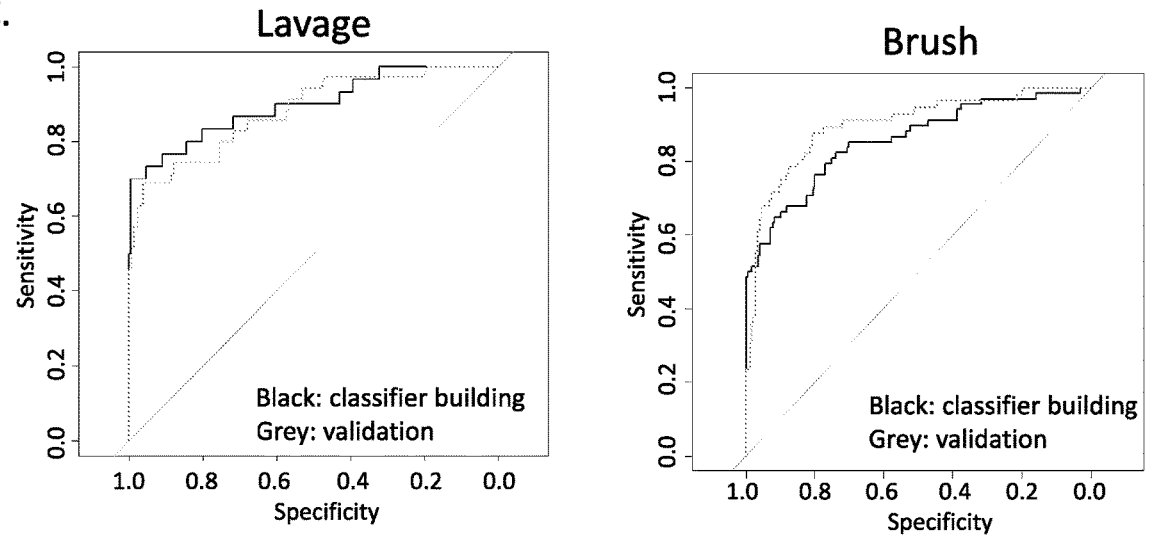

Figure 5
A. qMSP results in scrapes and urine
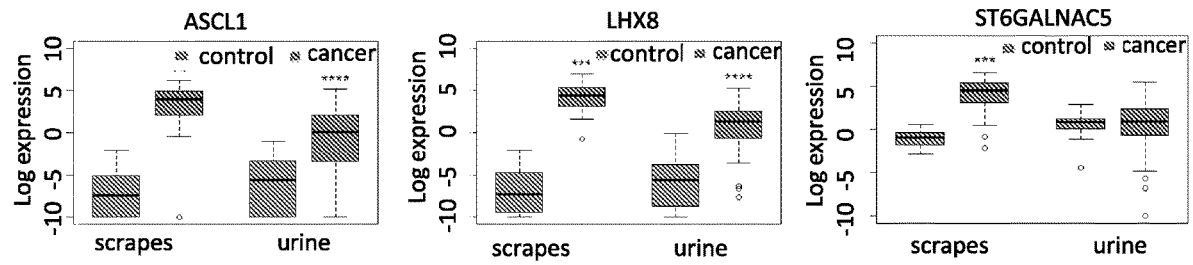
B. Receiver Operating Characteristics (ROC) curves in HPV+ scrapes
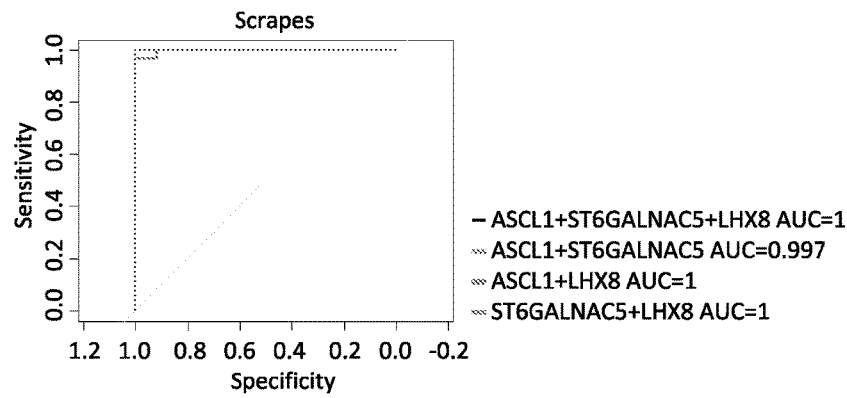
C. Receiver Operating Characteristics (ROC) curves in urine
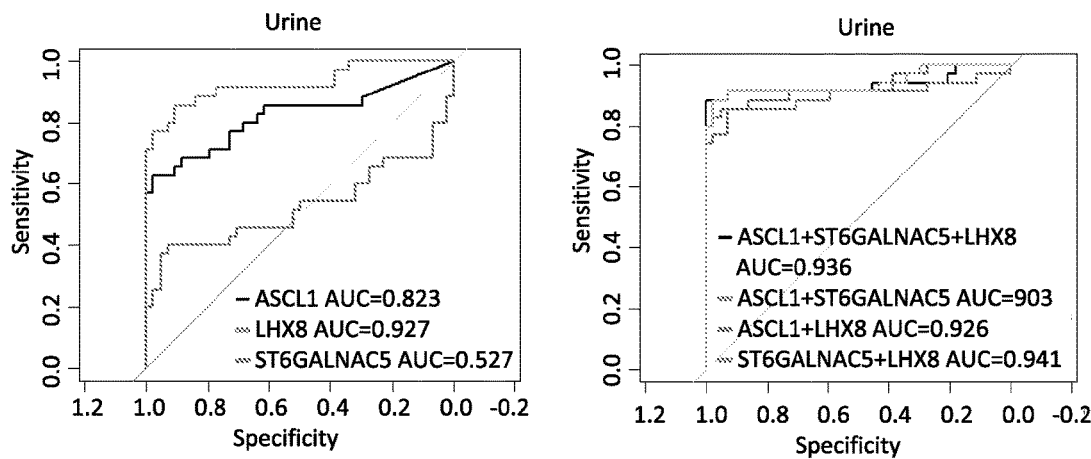

qMSP results in cervical scrapes of patients with endometrial cancer

Figure 7: ZNF-582 sequence (regulatory region and exon1) derived from Refseq NM_144690 (hg19). The coding sequence is in upper case and underlined is the CpG rich region. (SEQ ID NO: 25)

```
>hg19_refGene_NM_144690
agttcaggcattctggctccagtcttagagatggttaagggttcacactc
ttaaccatttattacaccatagagctcaccaggtttgagggaaacaggat
caaatcaaaagagtcactcaggactccagtcctcactcaaggacaaactg
ttccacctcggacagggagagtttccgcattctgagacccagcataacag
gtcctgaccggcatctggcactcggactcccaatcatactggatcacact
ggctcgggatgtgtaaagtccagggcttctcatttgatgacaccaaag
ccgcctaaaacaagagagaattaacaactacctacggcggtctgatatt
tgcccaagagatgccgccccataaaactcctttacatctttataacgttt
ttattttgcgttctccttcataacccacatttaactcaccatagatgtaa
tgtttaaaattagttaccagataaactcttacgcttccaaactttaaggt
tccttcgaaaccttctggtaaaactgttgttccacggaaatgggaacgta
acggatgaggcaatcttccacagccgcacacagttgtgtatccaccgcta
aacggtcccagtcatacattcaacgacccacgcggagtcagaagctacca
ccacacactgtcaaaatcacgcacacagtgacggccccttgcccactc
ggtcactcgcccacaatctctcgctagagaatcacacgcagatagcacac
ccagcaccacagacccaggaagcaacccagggactcgaacacacgaaca
gcactcctccgcgcactgcgcaggcacgcctgcgtccggctcaccctgaa
acatcgcgagatccggcttcaaggccgggctgctgcctttacgcctaaag
actatgtttccggaagacactgcggcgccggccctatcatggcgcagca
tcggtgtctttgtgcgtctgcgccatcttccggctgcgcacggcgaatc
CACCGGTACCGTGGTGGAAGCGCGCCCTGGGCTGCCGGGGCGCGGCCGC
GGTGGCACTTGGACCCGAGGAGGCGGCAG
```

Figure 8: ZIC1 promoter region and coding sequence (derived from Refseq: NM_003412 (hg19)); CpG islands in grey and coding sequence in UPPER CASE (SEQ ID NO: 26)

qMSP results in vulvar specimens qMSP results in anal specimens

METHYLATION CLASSIFIER FOR DETECTION OF HPV-INDUCED INVASIVE CANCERS, NONHPV-INDUCED GYNAECOLOGICAL AND ANOGENITAL CANCERS AND THEIR HIGH-GRADE PRECURSOR LESIONS

A methylation classifier for detection of HPV-induced invasive cancers, nonHPV-induced gynaecological and anogenital cancers and their high-grade precursor lesions

CROSS-REFERENCE TO RELATED PATENT APPLICATIONS

This application is a U.S. National Stage Application under 35 U.S.C. § 371 of International Patent Application No. PCT/NL2018/050143, filed Mar. 9, 2018, which claims the benefit of priority of European Patent Application number 17160346.7 filed Mar. 10, 2017, both of which are incorporated by reference in their entireties. The International Application was published on Sep. 13, 2018, as International Publication No. WO 2018/164577 A1.

SEQUENCE LISTING

A sequence listing, created on Sep. 5, 2019 as the ASCII text file "P114691PC00 Sequence listing.txt" having a file size of 18.3 kilobytes, is incorporated herein by reference in its entirety.

FIELD OF THE INVENTION

The invention relates to the field of cancer prevention and medical diagnostics; and is concerned with a molecular diagnostic assay for cancers, especially human papillomavirus (HPV)-induced invasive cancers and high-grade precursor lesions thereof, such as invasive cervical cancer and premalignant cervical lesions, nonHPV-induced gynaecological and anogenital cancers. In particular, the present invention relates to the use of a methylation classifier based on the genes LHX8, ASCL1 andST6GALNAC5 and their regulatory sequences as marker for hrHPV-induced invasive cancers, nonHPV-induced gynaecological and anogenital cancers and their premalignant lesions with invasive potential.

BACKGROUND OF THE INVENTION

Cancer of the uterine cervix is the fourth most common cancer in women world-wide and is responsible for approximately 250.000 cancer deaths a year.

Cervical squamous cell carcinoma development is characterized by a sequence of premalignant lesions, so-called cervical intraepithelial neoplasia (CIN), which are graded 1 to 3, referring to mild dysplasia (CIN 1), moderate dysplasia (CIN 2) and severe dysplasia/carcinoma in situ (CIN 3), respectively. CIN 1 is also referred to as low grade squamous intraepithelial lesion (LSIL) and CIN 2 and CIN 3 together as high grade squamous intraepithelial lesion (HSIL). For cervical adenocarcinoma, adenocarcinoma in situ (ACIS) is an established precursor lesion. In principle, these premalignant lesions are reversible, although the more severe the lesion, the lower the chance of spontaneous regression. Cervical cancer is considered a preventable disease because the premalignant stages can be detected by exfoliative cytology and treated relatively easily when necessary, with only minor side effects. Cervical screening is aimed to early diagnose the high-grade premalignant (i.e., CIN 2/3 and adenocarcinoma in situ) and treatable cancerous lesions, thereby reducing the mortality of invasive cervical cancer. General medical practice comprises the treatment of all women with morphologically confirmed CIN 2, CIN 3 and adenocarcinoma in situ, in order to prevent the development of cervical cancer.

Over the past decade it has been well established that cervical carcinogenesis is initiated by an infection with high-risk human papillomavirus (hrHPV). Expression of the viral oncogenes E6 and E7, which disturb the p53 and Rb tumor suppressor pathways, respectively, has been shown to be essential for both the onset of oncogenesis and the maintenance of a malignant phenotype. Therefore, testing for hrHPV appeared as an attractive, primary screening tool. However, consistent with a multistep process of carcinogenesis, additional alterations in the host cell genome are required for progression of an hrHPV infected cell to invasive cancer cell. Only a small proportion of women infected with high-risk HPV will develop high-grade premalignant cervical lesions (CIN 2/3) and, if left untreated, cervical cancer. In most women with premalignant cervical lesions the lesions regress spontaneously. Of the women who participate in population based screening, about 5-6% have a positive hrHPV test. However, only at maximum 20% of them (1% of the participating women) have CIN 2/3. Therefore, primary screening by hrHPV testing will be accompanied with a substantial number of redundant follow-up procedures and unnecessary anxiety amongst women, unless markers can be applied to the cervical smears that allow stratification of hrHPV positive women for risk of CIN 2/3 and adenocarcinoma in situ.

A major challenge is to reduce the percentage of HPV test positive women to those that have clinically meaningful lesions. One mode is to use cytology as a secondary (so-called triage) test for hrHPV positive women. Still, this leaves a substantial number of hrHPV positive women with normal cytology (3.5% of the women in the screening population), of which still 10% have or acquire CIN 3. Moreover, cytology is not an option for self-sampled cervico-vaginal specimens that can be taken at home, since these are not representative for the cytological status of the cervix. Another mode is to use HPV16/18 genotyping. This however leaves women with non-HPV16/18 types who are, although to a lesser extent, also at risk of CIN 2/3 and adenocarcinoma in situ. Therefore, there is a need for supplementary or alternative triage tools to stratify hrHPV positive women into those with and without CIN 2/3 and adenocarcinoma in situ.

Primary screening for cervical cancer using disease markers based on host cell changes in cancer genes provides a promising alternative provided that specificity and sensitivity is sufficiently high. This option is of particular interest for low and middle income countries, where quality-controlled cytology is absent and implementation of follow-up algorithms for HPV-positive women is complicated. In these countries self-sampling has shown to facilitate access to cervical screening (Laczano-Ponce et al., Lancet. 2011; 378: 1868-1873). In this sense it is extremely useful to have markers that also prevail in self-samples. It appears that there is a huge difference in the 'behaviour' of markers on vaginal smears that have been obtained by medical skilled personnel like doctors or nurses and on vaginal swabs that have been collected by the woman herself. It has appeared that many markers that would be suitable for doctor-provided samples are not useful in self-samples. The necessity to work with self-samples instead of doctor samples is high in low and middle income countries since in those countries there is less medical personnel per capita and often there is a cultural problem by letting other persons taking a vaginal sample. Further, even in highly developed countries self-sampling is an ideal way to reduce the costs of obtaining vaginal samples for large scale cervical cancer screening. An even higher acceptance rate can be expected when urine samples can be used for early cancer detection.

Endometrial cancer is the most common gynaecologic malignancy in many developed countries (Siegel et al., CA Cancer J. Clin., 64 (2014), pp. 9-29). Early stage endometrial cancer has a very good prognosis. Therefore, early detection will increase the chance of cure and avoid or reduce cumbersome and costly therapeutic intervention. As shedding of tumor cells in cervical scrapes has been demonstrated, early detection of endometrial cancer by non-invasive sampling is feasible. However, conventional cytology on cervical scrapes has a very low sensitivity for detection of endometrial cancer. Testing for molecular alterations, such as DNA methylation, associated with endometrial cancer, may provide a promising approach for early detection of endometrial cancer (de Strooper et al., J Clin Pathol. 2014; 67(12):1067-71, Bakkum-Gamez et al. *Gynecol Oncol*. 2015; 137(1):14-22). Similarly, testing for cancer specific DNA alterations in cervical scrapes for the detection of ovarian cancer has recently been proposed (Kindle et al., Sci Transl Med. 2013; 5(167):1-21).

SUMMARY OF THE INVENTION

The inventors now have found a method for detecting HPV-induced invasive cancers, nonHPV-induced gynaecological and anogenital cancers, and their high-grade precancerous lesions wherein said method comprises the detection of hypermethylation in the gene sequence of LHX8, ASCL1 and ST6GALNAC5 or in the regulatory sequence of these genes in a cell whereby such hypermethylation indicates the presence of HPV-induced precursor lesions with invasive potential, HPV-induced invasive cancers and/or nonHPV-induced gynaecological and anogenital cancers. Preferably, in such a method said HPV-induced high-grade precancerous lesion or HPV-induced invasive carcinoma is a high-grade premalignant cervical lesion or invasive cervical cancer, more preferably a high-risk HPV-induced invasive cancer. Preferably, said nonHPV-induced gynaecological cancer is a endometrial cancer. Preferably said nonHPV-induced anogenital cancer is a vulvar or penile cancer.

Also comprised in the present invention is a method for detecting vulva cancer and vulvar HPV-induced precursor lesions with invasive potential, said method comprising detection of a methylation classifier consisting of ASCL1 and one or more of ZIC1, ZNF-582 and LHX8 sequences in a cell whereby such hypermethylation indicates the presence of vulva cancer and vulvar HPV-induced precursor lesions with invasive potential.

Further comprised in the invention is a method for detecting anal cancer and anal HPV-induced precursor lesions with invasive potential, said method comprising detection of a methylation classifier consisting of ASCL1 and one or more of ZIC1 and ZNF-582 sequences in a cell whereby such hypermethylation indicates the presence of anal cancer and anal HPV-induced precursor lesions with invasive potential.

Also part of the invention is a method for the detection of ovarian cancer and ovarian precursor lesions, said method comprising detection of a methylation classifier consisting of ASCL1, and one or more of LHX8 and ZIC1 sequences in a cell whereby such hypermethylation indicates the presence of ovarian cancer and ovarian precursor lesions.

In a preferred embodiment of the invention the hypermethylation is detected in the sequences as indicated in FIGS. 1, 2, 3, 7 and 8. In a further preferred embodiment said hypermethylation is an increased methylation of the methylation classifier LHX8, ASCL1, ZNF-582, ZIC1 and ST6GALNAC5 CpG rich promoter and/or gene sequences, such as regulatory sequences, in a test cell as compared to a comparable normal cell In a preferred embodiment of the invention the detection of (hyper)methylation is performed by using a methylation sensitive restriction endonuclease, chosen from the group consisting of BssHII, MspI, NotI and HpaII. In another preferred embodiment of the invention the detection of (hyper)methylation is performed using nanotechnology.

In an alternative preferred embodiment of the invention, the detection of (hyper)methylation is performed via a methylation specific PCR, which is based on bisulfite modification of DNA, followed by specific PCR reactions that target CpG rich sequences. Preferably in such a method the reagent is a nucleic acid probe or primer that binds to the nucleic acid as indicated in FIG. 1, 2 or 3, and more preferably said nucleic acid probe or primer has a detectable label.

In another embodiment of the invention the nucleic acid probe has a nucleotide sequence selected from the group consisting of:
  a) a polynucleotide sequence capable of hybridizing under stringent conditions to the sequence ASCL1 as set forth in FIG. 1 or to the sequence LHX8 as set forth in FIG. 2 or to the sequence ST6GALNAC5 as set forth in FIG. 3; or to the sequence ZIC1 as set forth in FIG. 8 or to the sequence ZNF-582 as set forth in FIG. 7;
  b) a polynucleotide having at least 70% identity to the polynucleotide of a);
  c) a polynucleotide complementary to the polynucleotide of a); and
  d) a polynucleotide comprising at least 15 bases of a nucleotide of a) or b).

Further preferred in the present method of the invention the methylation of the gene sequence of LHX8, ASCL1, ZNF-582, ZIC1 and ST6GALNAC5 or the regulatory sequence of these genes is determined.

Also part of the invention is the use of LHX8, ASCL1, ZNF-582, ZIC1 and ST6GALNAC5 as a molecular diagnostic marker for the detection of HPV-induced invasive carcinoma, nonHPV-induced gynaecological or anogenital carcinoma, and their high-grade precancerous lesion. Further part of the invention is the use of the methylation classifier LHX8, ASCL1, and ST6GALNAC5 as a molecular diagnostic marker for the detection of HPV-induced high-grade precancerous lesion or HPV-induced invasive carcinoma or nonHPV-induced gynaecological or anogenital cancer, preferably wherein the methylation of said marker is predictive for the occurrence of said lesion, carcinoma or cancer. Also part of the invention is the use of the methylation classifier ASCL1, and one of ZIC1, ZNF-582 and LHX8 as a molecular diagnostic marker for the detection of vulva cancer or vulvar HPV-induced high-grade precancerous lesion, preferably wherein the methylation of said marker is predictive for the occurrence of said lesion or cancer. Further part of the invention is the use of the methylation classifier ASCL1, and one of ZIC1 and ZNF-582 as a molecular diagnostic marker for the detection of anal cancer or anal HPV-induced high-grade precancerous lesion, preferably wherein the methylation of said marker is predictive for the occurrence of said lesion or cancer. Next, part of the invention is formed by the use of the methylation classifier ASCL1, and one of LHX8 and ZIC1 as a molecular diagnostic marker for the detection of ovarian cancer, preferably wherein the methylation of said marker is predictive for the occurrence of said cancer.

The invention also comprises a kit of parts for use in a method of detecting HPV-induced invasive carcinoma, non-HPV-induced gynaecological or anogenital carcinoma and their high-grade precancerous lesion said kit comprising
- means for the detection of LHX8, ASCL1 and ST6GALNAC5 methylation wherein said means comprise probes and/or primers specific for the ASCL1 nucleotide sequence of FIG. 1 and the LHX8 nucleotide sequence of FIG. 2 and the ST6GALNAC5 nucleotide sequence of FIG. 3;
- means for the detection of ASCL1 and ST6GALNAC5 methylation wherein said means comprise probes and/or primers specific for the ASCL1 nucleotide sequence of FIG. 1 and the ST6GALNAC5 nucleotide sequence of FIG. 3; or
- means for the detection of ASLCL1 and LHX8 methylation wherein said means comprise probes and/or primers specific for the ASCL1 nucleotide sequence of FIG. 1 and the LHX8 nucleotide sequence of FIG. 2, or
- means for the detection of ASCL1 and at least one of ZIC1, ZNF-582 and LHX8 wherein said means comprise probes and/or primers specific for the ASCL1 nucleotide sequence of FIG. 1 and either of the ZNF-582 nucleotide sequence of FIG. 7, the ZIC1 nucleotide sequence of FIG. 8 and/or the LHX8 nucleotide sequence of FIG. 2;

The kit preferably further comprises—means for the detection of HPV infection, wherein said means comprise probes and primers specific for HPV.

BRIEF DESCRIPTION OF THE DRAWINGS

FIG. 1 shows the ASLC1 promoter region and CpG rich sequence exon 1; the coding sequence is given in upper case.

FIG. 2 shows the LHX8 5' regulatory region and coding sequence (exon 1). The coding sequence is in upper case.

FIG. 3 shows the ST6GALNAC5 5' regulatory region, coding sequence (exon 1 and 2) and intron 1. The coding sequence is in upper case.

FIG. 4 shows boxplots of the methylation levels of LHX8, ASCL1 and ST6GALNAC5 in hrHPV-positive self-collected cervico-vaginal specimens as measured by quantitative methylation specific PCR (qMSP) in lavage samples (A) and brush self samples (B). In qMSP analysis the methylation values of the targets are normalised to reference gene ACTB using the comparative Ct method ($2^{-\Delta Ct}$). On the y-axes levels of methylated DNA are presented; on the x-axes groups represent controls (i.e. women with ≤CIN1), women with CIN2, CIN3, and squamous cervical cancer. The levels of methylation of LHX8, ASCL1 and ST6GALNAC5 increases with the severity of the disease and are significantly increased in CIN3 and SCC compared to controls. Significant differences in methylation levels between groups are indicated, * indicates <0.05,  indicates <0.005, * indicates <0.0005. C shows Receiver Operating Characteristics (ROC) curves.

FIG. 5 A shows boxplots of the methylation levels of LHX8, ASCL1 and ST6GALNAC5 cervical scrapes and urine of controls (i.e. women with sCIN1) and women with cervical cancer as measured by quantitative methylation specific PCR (qMSP). In qMSP analysis the methylation values of the targets are normalised to reference gene ACTB using the comparative Ct method ($2^{-\Delta Ct}$). On the y-axes levels of methylated DNA are presented; on the x-axes groups represent controls (green; women with sCIN1) and women with cervical cancer (red). The levels of methylation of LHX8, ASCL1 and ST6GALNAC5 are significantly increased in both scrapes and urine of women with cervical cancer compared to controls. Significant differences in methylation levels between groups are indicated, * indicates <0.05,  indicates <0.005, * indicates <0.0005. B. shows Receiver Operating Characteristics (ROC) curve of any marker combination in hrHPV+ cervical scrapes, showing that a combination of markers enables the detection of all cancers at highest specificity. C. shows Receiver Operating Characteristics (ROC) curve of individual markers (left) and any marker combination in urine, showing that a combination of 3 markers enables the detection of all cancers at highest specificity.

FIG. 7 shows the ZNF-582 5' regulatory region and coding sequence (exon 1). The coding sequence is in upper case.

FIG. 8 shows the ZIC1 5' regulatory region and coding sequence (exon 1). The coding sequence is in upper case.

DETAILED DESCRIPTION OF THE INVENTION

Figure 6:
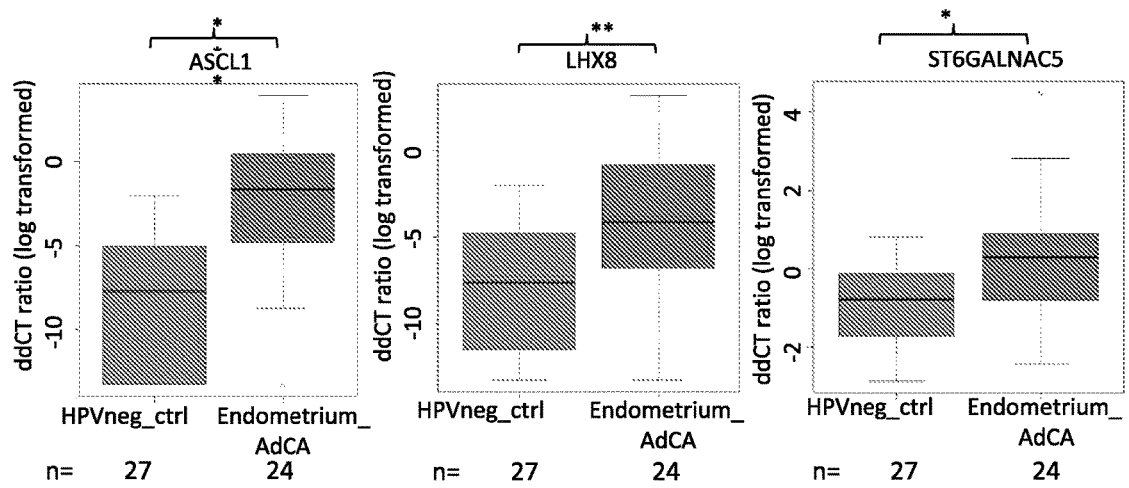
FIG. 6 shows the boxplots of the methylation levels of LHX8, ASCL1 and ST6GALNAC5 in cervical scrapes of women with endometrial cancer as measured by quantitative methylation specific PCR. In qMSP analysis the methylation values of the targets are normalised to reference gene ACTB using the comparative Ct method ($2^{-\Delta Ct}$). On the y-axes levels of methylated DNA are presented; on the x-axes groups represent control women and women with endometrial cancer. The levels of methylation of LHX8, ASCL1 and ST6GALNAC5 are significantly increased in women with endometrial cancer compared to controls

The term "HPV-induced invasive cancer" refers to a carcinoma induced by high-risk HPV, which invades surrounding tissue. This includes all HPV-induced carcinoma histotypes, i.e., squamous cell carcinomas, adenocarcinomas, adenosquamous carcinomas and neuroendocrine carcinomas in relevant organs such as cervix, oral cavity, oropharynx, anus, rectum, penis, vulva, vagina, etc. It especially includes head and neck squamous cell carcinomas (HNSCC), cervical squamous cell carcinomas and cervical adenocarcinomas.

The term "invasive cervical cancer" refers to a cervical carcinoma invading surrounding tissue. This includes all carcinoma histotypes, i.e., squamous cell carcinomas, adenocarcinomas, adenosquamous cell carcinomas and neuroendocrine carcinomas.

The term "nonHPV-induced gynaecological or anogenital cancer" refers to endometrial cancer, ovarian cancer, vulvar cancer, vaginal cancer, anal cancer and penile cancer that are HPV-negative.

The terms "premalignant lesion" and "precursor lesion" refer to a stage in the multistep cellular evolution to cancer with a strongly increased chance to progress to a carcinoma. With classical morphology the pathologist is unable to predict in the individual patient which of these lesions will progress or regress. The current patent refers to a method, which can predict invasive cancer or a high-grade precursor lesion thereof.

The term "high-grade premalignant cervical lesion" refers to a stage in the multistep cellular evolution to cervical cancer with a strongly increased chance to progress to a cervical carcinoma. The term "capable of specifically hybridizing to" refers to a nucleic acid sequence capable of specific base-pairing with a complementary nucleic acid sequence and binding thereto to form a nucleic acid duplex.

A "complement" or "complementary sequence" is a sequence of nucleotides which forms a hydrogen-bonded duplex with another sequence of nucleotides according to Watson-Crick base-paring rules. For example, the complementary base sequence for 5'-AAGGCT-3' is 3'-TTCCGA-5'.

The term "stringent hybridization conditions" refers to hybridization conditions that affect the stability of hybrids, e.g., temperature, salt concentration, pH, formamide concentration and the like. These conditions are empirically optimised to maximize specific binding and minimize non-specific binding of the primer or the probe to its target nucleic acid sequence. The terms as used include reference to conditions under which a probe or primer will hybridise to its target sequence, to a detectably greater degree than other sequences (e.g. at least 2-fold over background). Stringent conditions are sequence dependent and will be different in different circumstances. Longer sequences hybridise specifically at higher temperatures. Generally, stringent conditions are selected to be about 5° C. lower than the thermal melting point ($T_m$) for the specific sequence at a defined ionic strength and pH. The $T_m$ is the temperature (under defined ionic strength and pH) at which 50% of a complementary target sequence hybridises to a perfectly matched probe or primer. Typically, stringent conditions will be those in which the salt concentration is less than about 1.0 M Na ion, typically about 0.01 to 1.0 M Na ion concentration (or other salts) at pH 7.0 to 8.3 and the temperature is at least about 30° C. for short probes or primers (e.g. 10 to 50 nucleotides) and at least about 60° C. for long probes or primers (e.g. greater than 50 nucleotides). Stringent conditions may also be achieved with the addition of destabilizing agents such as formamide. Exemplary low stringent conditions or "conditions of reduced stringency" include hybridization with a buffer solution of 30% formamide, 1 M NaCl, 1% SDS at 37° C. and a wash in 2×SSC at 40° C. Exemplary high stringency conditions include hybridization in 50% formamide, 1 M NaCl, 1% SDS at 37° C., and a wash in 0.1×SSC at 60° C. Hybridization procedures are well known in the art and are described in e.g. Ausubel et al, Current Protocols in Molecular Biology, John Wiley & Sons Inc., 1994.

The term "oligonucleotide" refers to a short sequence of nucleotide monomers (usually 6 to 100 nucleotides) joined by phosphorous linkages (e.g., phosphodiester, alkyl and aryl-phosphate, phosphorothioate), or non-phosphorous linkages (e.g., peptide, sulfamate and others). An oligonucleotide may contain modified nucleotides having modified bases (e.g., 5-methyl cytosine) and modified sugar groups (e.g., 2'-O-methyl ribosyl, 2'-O-methoxyethyl ribosyl, 2'-fluoro ribosyl, 2'-amino ribosyl, and the like). Oligonucleotides may be naturally-occurring or synthetic molecules of double- and single-stranded DNA and double- and single-stranded RNA with circular, branched or linear shapes and optionally including domains capable of forming stable secondary structures (e.g., stem-and-loop and loop-stem-loop structures).

The term "primer" as used herein refers to an oligonucleotide which is capable of annealing to the amplification target allowing a DNA polymerase to attach thereby serving as a point of initiation of DNA synthesis when placed under conditions in which synthesis of primer extension product which is complementary to a nucleic acid strand is induced, i.e., in the presence of nucleotides and an agent for polymerization such as DNA polymerase and at a suitable temperature and pH. The (amplification) primer is preferably single stranded for maximum efficiency in amplification. Preferably, the primer is an oligodeoxy ribonucleotide. The primer must be sufficiently long to prime the synthesis of extension products in the presence of the agent for polymerization. The exact lengths of the primers will depend on many factors, including temperature and source of primer. A "pair of bi-directional primers" as used herein refers to one forward and one reverse primer as commonly used in the art of DNA amplification such as in polymerase chain reaction (PCR) amplification.

The term "probe" refers to a single-stranded oligonucleotide sequence that will recognize and form a hydrogen-bonded duplex with a complementary sequence in a target nucleic acid sequence analyte or its cDNA derivative.

DNA methylation is a biochemical process that is important for normal development in higher organisms. It involves the addition of a methyl group to the 5 position of the cytosine pyrimidine ring or the number 6 nitrogen of the adenine purine ring. DNA methylation at the 5 position of cytosine has the specific effect of reducing gene expression and has been found in every vertebrate examined. In adult somatic tissues, DNA methylation typically occurs in a CpG dinucleotide context.

Using a genome wide DNA methylation screen on self-collected cervico-vaginal specimens and extensive evaluation of a large series of genes that are targeted by methylation in self-collected cervico-vaginal specimens of women with CIN3 and cervical cancer it has now been found that a methylation classifier consisting of the genes encoding achaete-scute family bHLH transcription factor 1 (further referred to as ASCL1; Genbank Accession NM_004316), the gene encoding LIM homeobox 8 (further referred to as LHX8; Genbank Accession NM_001001933), and the gene encoding ST6 N-Acetylgalactosaminide Alpha-2,6-Sialyltransferase 5 (further referred to as ST6GALNAC5; Genbank Accession NM_030965) and their regulatory sequences are important determinants of hr-HPV induced carcinogenesis. The genes LHX8, ASCL1 and ST6GALNAC5 and their regulatory sequences thus provide valuable markers to diagnose invasive cervical cancer and the high-grade precursor lesions thereof in different sampling types, i.e. cervical scrapes, self-collected cervicovaginal specimens, as well as urine specimens. Additionally, the present invention is suited to diagnose non-cervical hrHPV-associated invasive cancers and their high-grade precursor lesions. Moreover, their methylation is additionally suited to diagnose endometrial and other nonHPV-induced gynaecological and anogenital cancers.

Further genes that have been found useful for detection of these kinds of hrHPV associated cancers and precancerous lesions are ZIC1 and ZNF-582.

The ZIC1 gene encodes a 48 kDa protein that functions as a transcription factor and is a member of the ZIC family of C2H2-type zinc finger proteins. Members of this family are important during development. ZIC1 is involved in neurogenesis. It plays important roles in the early stage of organogenesis of the CNS, as well as during dorsal spinal cord development and maturation of the cerebellum (reviewed by Grinberg and Millen, Clin Genet. 2005, 67(4): 290-6). ZIC1 hypermethylation has been described in colorectal, gastric, ovarian and hepatocellular cancer (Gan et al., PLoS One. 2011, 6(2):e16916; Wang et al., Biochem Biophys Res Commun. 2009,379(4):959-63; Huang et al., Epigenetics. 2013, 8(6):624-34; Wang et al., Tumour Biol. 2014, 35(8):7429-33). It has been mentioned as one of the factors that was found in a screen of hypermethylated genes in carcinoma in situ and cancer in a cervical swab (Wang et al., Cancer Med. 2015, 4(1):43-55) but only as one out of more than 2200 genes. Further, in our earlier application WO 2017/034407 it has been described that ZIC1 and GHSR promoter methylation are important determinants of hr-HPV induced carcinogenesis. The ZIC1 and GHSR genomic and regulatory sequences thus provide valuable markers to diagnose invasive cervical cancer and the high-grade precursor lesions thereof.

ZNF-582 is a member of the KRAB-ZNF family and these family members function as corepressors of gene transcription in biological processes related to DNA damage response, proliferation, cell cycle control and neoplastic transformation (Urrutia 2003; Genome Biol. 4: 231). This marker is found to be methylated in acute myeloid leukemia (Figueroa et al. 2010; Cancer Cell. 17: 13-27) and has also been described in cervical cancer (Huang et al. 2012; PLOS one. 7: e41060).

Cervical cancer is almost exclusively associated with human papillomavirus (HPV) infection. Human papillomaviruses, constitute a group of more than 150 types of viruses, as identified by variations in DNA sequence. The various HPVs cause a variety of cutaneous and mucosal diseases. HPVs are broadly classified into low-risk and high-risk types, based on their ability to induce malignant changes in infected cells. Low risk HPV types such as 1, 2, 4, 6, 11, 13 and 32 are primarily associated with benign lesions or common warts, while the high risk types, such as 16, 18, 31, 33, 35, 39, 45, 51, 52, 56, 58, 59, 66, and 68 are primarily associated with premalignant and malignant epithelial lesions. The high-risk HPV types have been found to cause invasive carcinoma of the uterine cervix, as well as invasive carcinoma elsewhere in the anogenital tract and/or head-neck region. Therefore, the present invention is not only suited to detect invasive cervical cancer and precursor stages thereof, but also other invasive cancers and corresponding precursor stages that are induced by HPV, particularly of the high-risk type. Thus, the present invention provides a method for the risk assessment of any HPV-induced high-grade premalignant lesion or invasive cancer.

Very suitable HPV-induced precursor lesions and invasive cancers in the context of the present invention are cervical precancerous lesions and invasive cervical cancers, but also precursor lesions and invasive cancers induced by high-risk HPV in other tissues such as oral cavity, oropharynx, anus, rectum, penis, vulva, vagina, etc.

As stated above, the methylation classifier consisting of methylation markers ASCL1, LHX8, and ST6GALNAC5 are also capable of detecting nonHPV-induced precursor lesions and invasive cancers. In the context of the present invention such cancers preferably are endometrial cancer, ovarian cancer, vulvar cancer, vaginal cancer, anal cancer and penile cancer.

A test cell may be a (pre)neoplastic cell, a proliferating cervical cell, or any other cell wherein the presence of an HPV-induced precursor lesion with invasive potential, HPV-induced invasive cancer, nonHPV-induced gynaecological and anogenital cancer is to be detected.

The ASCL1 marker is a proneural transcription factor and functions as a main regulator at the onset of differentiation in neurogenesis (Vasconcelos et al. 2014; Front. Cell. Neurosci. 8: 412). ASCL1 is found to be methylated in oral and colorectal cancer (Jin et al. 2009; Cancer Res. 69:7412-21; Li et al. 2015; Epigenetics 10:229-36). The LHX8 marker functions as a highly conserved transcription factor to regulate cell fate in neurogenesis, tooth morphogenesis and oogenesis (Zhou et al. 2015; FASEB J.; 29:4083-91). Methylation of LHX8 has been described for cervical, breast, and colorectal cancer (Tommasi et al. 2009; Breast cancer Res. 11: R14; Øster, B. et al. 2011; Int. J. Cancer 129:2855-66; Farkas et al. 2013; Epigenetics 8:1213-25; Boers et al. 2016; Clin. Epigenetics 8:29).

The ST6GALNAC5 marker is a transmembrane sialyl-transferase involved in the biosynthesis of gangliosides on the cell surface. (Drolez et al. 2016; Int. J. Mol. Sci. 17:1309). Methylation of ST6GALNAC5 has been described for cervical, breast, and colorectal cancer (Tommasi et al. 2009; Breast cancer Res. 11: R14; Øster, B. et al. 2011; Int. J. Cancer 129:2855-66; Farkas et al. 2013; Epigenetics 8:1213-25; Boers et al. 2016; Clin. Epigenetics 8:29).

Although individual markers have been described as methylated in cervical cancer, their diagnostic value to detect cervical cancer and CIN3 upon testing cervical material obtained by any sampling method, collected using any self-sampling device, urine and cervical scrapes is novel. More importantly, the three genes surprisingly are complementary to each other in terms of cervical cancer and CIN3 detection across all sample types. It is found that the ST6GALNAC5 marker which has an intermediate diagnostic performance enables the detection of individual lesions that are not detected by the markers LHX8 and/or ASLC1. Also the latter two show complementarity to each other as found upon logistic regression analysis.

The present inventors have now established that detection of a methylation classifier based a combination of LHX8, ASCL1 and ST6GALNAC5 promoter methylation is a frequent event in cervical carcinomas of both squamous cell carcinoma, adeno-squamous carcinoma, adenocarcinoma and neuroendocrine carcinoma histotypes, and their high-grade precursor lesions. Most interestingly, the present inventors have shown that methylation classifier detecting hypermethylation of the genes LHX8, ASCL1 and ST6GALNAC5 and their regulatory sequences can be detected in both lavage-collected and brush collected cervico-vaginal self-samples but also in cervical scrapes collected by physicians and that this feature is able to predict the presence of a high-grade CIN lesion or invasive carcinoma. In addition, hypermethylation of the genes LHX8, ASCL1 and ST6GALNAC5 and their regulatory sequences can also be detected in urine specimens collected by self-sampling and LHX8, ASCL1 and ST6GALNAC5 methylation was found to be associated with the presence of an underlying high-grade CIN lesion or invasive cervical cancer.

Hypermethylation of the genes LHX8, ASCL1 and ST6GALNAC5 and their regulatory sequences can also be detected in HPV-positive and HPV-negative vulvar and anal cancers and their high-risk precursor lesions.

Moreover, detection of hypermethylation of the genes LHX8, ASCL1 and ST6GALNAC5 and their regulatory sequences is suited to diagnose endometrial, ovarian and other nonHPV-induced gynaecological and anogenital cancers.

Accordingly, the present invention provides a method for detecting HPV-induced high-grade precancerous lesions and HPV-induced invasive cancers, nonHPV-induced gynaecological and anogenital cancers such as endometrial and ovarian carcinoma, said method comprising detection of hypermethylation of the genes LHX8, ASCL1 and ST6GALNAC5 and their regulatory sequences in a cell whereby such hypermethylation indicates the presence of HPV-induced precursor lesions with invasive potential and HPV-induced invasive cancers and nonHPV-induced gynaecological and anogenital cancers such as endometrial carcinoma.

The test cell of the subject may comprise a cell from a sample of mucosal cells, such as cervical cells, and also other tissue such as oral cavity, oropharynx, penis, vulva, anus, rectum, endometrium, ovarium and other tissues wherein a precursor lesion or cancer associated with HPV or nonHPV-induced gynaecological, anogenital cancer or oropharyngeal cancer is to be detected. All such samples may be used as a sample in a method of the present invention. Preferably, a sample of a patient's cells comprise cervical cells or other epithelial cells of the anogenital or oropharyngeal tract as test cells. The cervical cells may e.g. be presented as a histological or cytological specimen. Cytological specimens comprise conventional cervical smears as well as thin layer preparations of cervical specimens and cervico-vaginal or vaginal specimens collected by self-sampling. Alternatively, cells may be presented in urine samples. A test cell wherein the present invention is especially advantageous over other known methods of detecting cancers in the cervix and adjacent tissues is a test cell obtained from a self-sample.

A method of the present invention is particularly suited for the detection of high-grade precancerous lesions and invasive cancers associated with LHX8, ASCL1 and ST6GALNAC5 that are induced by high-risk HPVs or derived from the (female) anogenital tract. A method of detecting HPV-induced high-grade precancerous lesions with invasive potential, HPV-induced invasive cancers and nonHPV-induced gynaecological and anogenital cancer may comprise measuring LHX8, ASCL1 and ST6GALNAC5 promoter.

FIG. 1 shows the CpG-rich promoter region of the ASCL1 gene as well as part of exon 1 of the coding sequence.

FIG. 2 shows the CpG-rich promoter region of the LHX8 gene as well as part of exon 1 the coding sequence.

FIG. 3 shows the CpG-rich promoter region of the ST6GALNAC5 gene as well as exon 1, intron 1 and part of exon 2 of the coding sequence.

The invention also comprises a method for detecting vulva cancer and vulvar HPV-induced precursor lesions with invasive potential, said method comprising detection of a methylation classifier consisting of ASCL1 and one or more of ZIC1, ZNF-582 and LHX8 sequences in a cell whereby such hypermethylation indicates the presence of vulva cancer and vulvar HPV-induced precursor lesions with invasive potential. As has been shown in the experimental part of the present invention the combination of ASCL1 with one or more of the mentioned gens forms a very useful methylation test panel for detecting these kind or cancers/lesions. Thus, also included is the use of the methylation classifier ASCL1, and one of ZIC1, ZNF-582 and LHX8 as a molecular diagnostic marker for the detection of vulva cancer or vulvar HPV-induced high-grade precancerous lesion, preferably wherein the methylation of said marker is predictive for the occurrence of said lesion or cancer.

Further, it has been demonstrated in the experimental part of the present invention that detection of a methylation classifier consisting of ASCL1 and one or more of ZIC1 and ZNF-582 sequences in a cell can be used to detect anal cancer and anal HPV-induced precursor lesions with invasive potential. In such a case, hypermethylation indicates the presence of anal cancer and anal HPV-induced precursor lesions with invasive potential. Thgus also part of the invention is formed by the use of the methylation classifier ASCL1, and one of ZIC1 and ZNF-582 as a molecular diagnostic marker for the detection of anal cancer or anal HPV-induced high-grade precancerous lesion, preferably wherein the methylation of said marker is predictive for the occurrence of said lesion or cancer.

Next, it has been shown that detection of a methylation classifier consisting of ASCL1, and one or more of LHX8 and ZIC1 sequences in a cell is very suitable for the detection of ovarian cancer and ovarian precursor lesions, whereby hypermethylation of the mentioned genes indicates the presence of ovarian cancer and ovarian precursor lesions. Accordingly, also the use of the methylation classifier ASCL1, and one of LHX8 and ZIC1 as a molecular diagnostic marker for the detection of ovarian cancer, preferably wherein the methylation of said marker is predictive for the occurrence of said cancer, is envisaged in the present invention.

Detection of methylation is performed on nucleic acid, such as DNA. The reagents that are used are typically a nucleic acid (DNA) probe or (PCR) primer or a restriction endonuclease, preferably a methylation sensitive restriction endonuclease for the detection of the presence of methyl groups on the test cell DNA.

The test cell component may be detected directly in situ or it may be isolated from other cell components by common methods known to those of skill in the art before contacting with the reagent (see for example, "Current Protocols in Molecular Biology", Ausubel et al. 1995. 4th edition, John Wiley and Sons; "A Laboratory Guide to RNA: Isolation, analysis, and synthesis", Krieg (ed.), 1996, Wiley-Liss; "Molecular Cloning: A laboratory manual", J. Sambrook, E. F. Fritsch. 1989. 3 Vols, 2nd edition, Cold Spring Harbor Laboratory Press)

Since examples presented show frequent methylation of the ASCL1 gene and regulatory sequence, it is desirable to directly determine whether the ASCL1 gene and regulatory sequence is hypermethylated. Similarly, it is also desirable to directly determine whether the LHX8 and ST6GALNAC5 gene and regulatory sequence is hypermethylated. In particular, the cytosine rich areas termed "CpG islands", which are primarily situated in the 5' regulatory regions of genes are normally unmethylated. The term "hypermethylation" includes any methylation of cytosine at a position that is normally unmethylated in the LHX8, ASCL1 and ST6GALNAC5 gene and regulatory sequence (e.g. the LHX8 and ASCL1 regulatory sequence and first exon and ST6GALNAC5 regulatory sequence, first exon, first intron and part of second exon, see FIGS. 1, 2 and 3, respectively). DNA methylation can be detected by the following assays currently used in scientific research:

- Methylation-Specific PCR (MSP), which is based on a chemical reaction of sodium bisulfite with DNA that converts unmethylated cytosines of CpG dinucleotides to uracil or UpG, followed by traditional PCR. However, methylated cytosines will not be converted in this process, and primers are designed to overlap the CpG site of interest, which allows one to determine methylation status as methylated or unmethylated.
- Whole genome bisulfite sequencing, also known as BS-Seq, which is a high-throughput genome-wide analysis of DNA methylation. It is based on aforementioned sodium bisulfite conversion of genomic DNA, which is then sequenced on a Next-generation sequencing platform. The sequences obtained are then re-aligned to the reference genome to determine methylation states of CpG dinucleotides based on mismatches resulting from the conversion of unmethylated cytosines into uracil.
- The HELP assay, which is based on restriction enzymes' differential ability to recognize and cleave methylated and unmethylated CpG DNA sites.
- ChIP-on-chip assays, which is based on the ability of commercially prepared antibodies to bind to DNA methylation-associated proteins like MeCP2.
- Restriction landmark genomic scanning, a complicated and now rarely-used assay based upon restriction enzymes' differential recognition of methylated and unmethylated CpG sites; the assay is similar in concept to the HELP assay.
- Methylated DNA immunoprecipitation (MeDIP), analogous to chromatin immunoprecipitation, immunoprecipitation is used to isolate methylated DNA fragments for input into DNA detection methods such as DNA microarrays (MeDIP-chip) or DNA sequencing (MeDIP-seq).
- Pyrosequencing of bisulfite treated DNA. This is sequencing of an amplicon made by a normal forward primer but a biatenylated reverse primer to PCR the gene of choice. The Pyrosequencer then analyses the sample by denaturing the DNA and adding one nucleotide at a time to the mix according to a sequence given by the user. If there is a mis-match, it is recorded and the percentage of DNA for which the mis-match is present is noted. This gives the user a percentage methylation per CpG island.
- Molecular break light assay for DNA adenine methyltransferase activity—an assay that relies on the specificity of the restriction enzyme DpnI for fully methylated (adenine methylation) GATC sites in an oligonucleotide labeled with a fluorophore and quencher. The adenine methyltransferase methylates the oligonucleotide making it a substrate for DpnI. Cutting of the oligonucleotide by DpnI gives rise to a fluorescence increase.
- Methyl Sensitive Southern Blotting is similar to the HELP assay, although uses Southern blotting techniques to probe gene-specific differences in methylation using restriction digests. This technique is used to evaluate local methylation near the binding site for the probe.
- Quantum-dot based methylation assay—an assay as described in Bailey, V. et al. (Genome Res. 19:1455-1461, 2009) in which the high specificity of MSP and the high sensitivity and simplicity of the quantum dot FRET (QD-FRET) technology (Zhang, C. et al., 2005, Nat. Mater. 4:826-831) is combined.
- DNA methylation detection using nanochip technology. This technique is able to detect DNA methylation at high sensitivity and specificity in minimal amounts of clinical material, without the need for bisulfite conversion and PCR amplification. Methods using solid states nanopores have been described by Shim, J. et al. (Sci. Rep. 3:1389, 2013). A device for lab on a chip technology is described in patent publication WO2009104967 (A1).

Hypermethylation preferably can be detected by methylation specific PCR, which is based on bisulfite modification of DNA, followed by specific PCR reactions that target CpG rich sequences.

An alternative preferred means to test for methylated sequences is by next generation sequencing of bisulfite modified DNA.

A third preferred means to detect methylated sequences and to discriminate between methylated and unmethylated DNA is based on nanotechnology.

For purposes of the invention a nucleic acid probe specific for LHX8, ASCL1 and/or ST6GALNAC5 may be used to detect the presence of LHX8, ASCL1 and/or ST6GALNAC5 polynucleotide (using nucleic acid probe) in biological fluids or tissues. Oligonucleotide primers based on any coding sequence region and regulatory sequence region in the LHX8, ASCL1 and/or ST6GALNAC5 sequence are useful for amplifying DNA, for example by PCR.

When using PCR primers, nucleic acid probes or restriction endonucleases, the 5' regulatory region and coding sequence of the LHX8 and, ASCL1 genes or the 5' regulatory region, coding sequence and first intron of ST6GALNAC5 sequence (as specified in FIGS. 1, 2 and 3 respectively) is analysed.

Any specimen containing a detectable amount of LHX8, ASCL1 and ST6GALNAC5 polynucleotide can be used. Preferred samples for testing according to methods of the invention include such specimens as (cervical or vaginal) scrapes, cervico-vaginal lavages or swabs, urine, blood and/or (cervical) biopsies and the like. Although the subject can be any mammal, preferably the subject is human.

Diagnostic methods for the detection of disorders, include methods wherein a sample for testing is provided, which sample comprises a cell preparation from cervical or other tissue. Preferably such samples are provided as smears or other cytological samples. Additional suitable samples include urine and blood.

A cell or tissue sample obtained from a mammal, preferably a human, is suitably pretreated to allow contact between the cellular DNA of a test cell comprised in said sample with a reagent that detects LHX8, ASCL1 and ST6GALNAC5 and detects an alteration in the methylation of the genes LHX8, ASCL1 and ST6GALNAC5 or their regulatory sequence as compared to that of a comparable normal cell. Samples may be mounted on a suitable support to allow observation of individual cells. Examples of well-known support materials include glass, polystyrene, polypropylene, polyethylene, polycarbonate, polyurethane, optionally provided with layers to improve cell adhesion and immobilization of the sample, such as layers of poly-L-lysine or silane. Cervical smears or biopsies may for instance be prepared as for the Papanicolaou (Pap) test or any suitable modification thereof as known by the skilled person, and may be fixed by procedures that allow proper access of the reagent to the target component. In certain embodiments of the invention the cytological specimens are provided as conventional smear samples or thin layer preparations of cervical cells or liquid based cytology samples or any other kind of preparation known to those of skill in the art. If storage is required, routine procedures use buffered formalin for fixation followed by paraffin embedding, which provides for a well-preserved tissue infrastructure.

In one embodiment of a method of the invention an increased methylation of the genes LHX8, ASCL1 and ST6GALNAC5 or their regulatory sequence in the test cell is detected as compared to the comparable normal cell.

The present invention also provides a kit of parts as defined in the claims, for use in a method of detecting HPV-induced precursor lesions with invasive potential, HPV-induced invasive cancers and nonHPV-induced gynaecological and anogenital cancers. Such a kit may suitably comprise a brush or spatula to take a (cervical) scrape either or not together with a container filled with collection medium to collect test cells. Alternatively, a sampling device consisting of an irrigation syringe, a disposable female urine catheter and a container with irrigation fluid will be included to collect cervical cells by cervico-vaginal lavage. Additionally or alternatively, a container to collect urine is suitable, preferably to be used to collect first-void urine. A kit according to the present invention further comprises primers and probes for the detection of LHX8, ASCL1 and ST6GALNAC5 gene or regulatory sequences.

A kit of parts according to the invention further comprises means for the detection of methylation of LHX8, ASCL1 and ST6GALNAC5 gene or regulatory sequence, such as, methylation-sensitive restriction enzymes, or probes or primers capable of hybridising to the nucleotide sequence of FIG. 1 and/or FIG. 2 and/or FIG. 3.

In yet another alternative embodiment of a kit of the invention the means for the detection of methylation of LHX8, ASCL1 and ST6GALNAC5 gene or regulatory sequence may be combined with means for the detection of HPV infection, preferably for the detection of HPV infection of the high-risk type. Such means may comprise HPV-specific primers or probes, protein markers for HPV infection or even surrogate markers for HPV infection as are known in the art.

The present invention will now be illustrated by way of the following, non limiting examples.

EXAMPLES

Example 1. Discovery of LHX8, ASCL1 and ST6GALNAC5 as Optimal Methylation Marker Panel to Detect Cervical Cancer and Precancer in Self-Samples A comprehensive analysis of genome-wide DNA methylation changes detectable in self-samples and associated with cervical carcinogenesis has been conducted by means of the Infinium 450K BeadChip array on hrHPV-positive self-samples. The sample series included consisted of 68 hrHPV-positive self-samples of 39 women with high-grade cervical intraepithelial neoplasia grade 3 (CIN3) and 29 women with low-grade cervical intraepithelial neoplasia grade 0 or 1 (sCIN1) The Infinium HumanMethylation450 BeadChip array analyses over 485,000 methylation sites per sample at single nucleotide resolution of the human genome (Illumina, San Diego, CA, USA). By this approach we identified 12 methylation targets that were specifically associated with the presence of CIN3. Next, the 12 most discriminative methylated genes were analysed using multiplex qMSP assays in two separate large series consisting of either hrHPV-positive lavage self-samples (n=245) or hrHPV-positive brush self-samples (n=246) from women with and without CIN3. In both lavage and brush self-samples, 11 of 12 selected genes showed significantly increased methylation levels (p<0.0005) in self-samples from women with CIN3 compared to hrHPV-positive controls (see also FIG. 4).

To subsequently build an optimal classifier of methylation markers which is universally applicable to any self-sample type, logistic regression analysis was performed on both lavage and brush self-sample qMSP datasets. Following backward elimination, the optimal methylation classifiers in both self-sample types were compared. The reason for testing both self-sampler types in order to find a methylation classifier that is universally applicable to self-collected cervico-vaginal specimens, independent of the collection device used, is based on previous research findings indicating that the clinical performance of methylation markers depends on the type of self-sampler used. For example it was found that methylation markers MAL and mir124-2 show a good clinical performance for the detection of CIN3+ in lavage self-samples, but not in brush-based self-samples. Surprisingly, in this study an optimal methylation classifier consisting of the genes ASCL1, LHX8 and ST6GALNAC5 and their regulatory sequence, was found for both self-sample types. Methylation levels of ASCL1, LHX8 and ST6GALNAC5 as detected in lavage and brush self-samples are shown in FIGS. 4A and 4B, respectively. Methylation levels of all 3 genes were significantly increased in women with CIN3 and extremely high in women with cervical cancer. The methylation classifier showed an excellent clinical performance for CIN3 detection in both hrHPV-positive lavage (AUC=0.90) and brush (AUC=0.86) self-samples. The methylation classifier scored 83% (25 of 30) of lavage self-samples and 76% (52 of 68) of brush self-samples from women with CIN3 methylation-positive with a corresponding specificity in hrHPV-positive controls of 80%. Importantly, virtually all women with cervical cancer tested positive for the methylation classifier. The clinical performance for detection of CIN3+(CIN3 and cancer) is superior to previously published methylation marker panels. The methylation classifier has a 79%-89% sensitivity and 75%-77% specificity for CIN3+ in lavage and brush self-samples. In comparison, the best currently available methylation panel tested on large self-sample series is FAM19A4/miR124-2, which has a sensitivity of 69-71% and a specificity of 68-76% for CIN3+ detection in both lavage and brush self-samples (De Strooper et al. *Gynecol. Oncol.* 141, 341-347 (2016)). Other marker panels, such as JAM3/EPB41L3/TERT/C13ORF18, have only been tested on small selected series of self-samples (Boers. et al. *Br. J. Cancer* 111, 1095-101 (2014); Eijsink et al. *Gynecol. Oncol.* 120, 280-283 (2011).)

Primers and probes used for LHX8, ASCL1 and ST6GALNAC5 qMSP analysis are listed in Table 1. The housekeeping gene ß-actin (ACTB) was chosen as a reference for total DNA input measurement. Quantification was performed using the comparative Ct method (Schmittgen et al., Nat Protoc 2008, 3:1101-1108).

Example 2 Validation of Methylation Classifier in Lavage and Brush Self-Samples

To validate the clinical performance of the methylation classifier, we analysed another, independent, large series of hrHPV-positive lavage self-samples (n=198) and brush self-samples (n=278) using a multiplex qMSP assay. The methylation classifier showed a good and comparable clinical performance for CIN3 detection as observed in the above described sample series, both for hrHPV-positive lavage (AUC=0.88) and brush (AUC=0.90) self-samples (see FIG. 4C for ROC curves). In the validation set, 74% (26 of 35) of lavage self-samples and 88% (49 of 56) of brush self-samples from women with CIN3 showed methylation-positivity with a corresponding specificity in hrHPV-positive controls of 79% and 81%, respectively.

Example 3. LHX8, ASCL1 and ST6GALNAC5 Methylation as Marker for Primary Screening in Self-Collected Cervico-Vaginal Specimens Methylation markers tested so far are not well suitable for use in primary screening due to a too low specificity at an acceptable sensitivity for CIN2/3 and cancer. When evaluating the use the methylation classifier consisting of LHX8, ASCL1 and ST6GALNAC5 as a marker for primary screening it was surprisingly found that upon analysis of HPV-negative self-samples and self-samples of women with CIN3, the classifier also has a very high AUC of 0.895 on lavage self-samples to detect CIN3 as well as on brush self-samples (AUC is 0.828).

The present findings show that a methylation classifier detecting hypermethylation of the genes LHX8, ASCL1 and ST6GALNAC5 and their regulatory sequence enables the detection of underlying CIN2+ not only when applied to self-collected cervico-vaginal lavage specimens but self-collected vaginal brush samples as well. The latter is a specimen type in which previous known markers often performed with low clinical sensitivity. Consequently, the LHX8, ASCL1 and ST6GALNAC5 markers can be considered as pan-detection markers showing equal performance independent of the sampling device used. Importantly, the high AUC values and specificity rates enable primary screening by testing the methylation classifier genes, obviating the need for initial hrHIPV testing. As described below (Example 6) such application also enables the detection of hrHPV-negative cancers that are missed in current screening settings.

Example 4: Detection of LHX8, ASCL1 and ST6GALNAC5 Methylation in hrHPV-Positive Cervical Scrapes From women participating in a population-based screening we studied cervical scrapes of hrHPV positive women in which CIN3 (n=56) was diagnosed, and hrHPV negative and positive women in whom at maximum CIN 1 was diagnosed (n=40 and n=87, respectively). Additionally, cervical scrapes of women diagnosed with squamous cell carcinoma (SCC;n=23) and adenocarcinoma (AdCa;n=3) of the cervix were tested. Cervical scrapes of these women were collected in preservation medium in which nucleic acids are well preserved.

LHX8, ASCL1 and ST6GALNAC5 methylation was significantly increased in scrapes of women with CIN3, SCC and AdCa compared to HPV negative and HPV positive controls. Receiver Operating Characteristics analysis showed an AUC of 0,890 to detect CIN3 in an HPV-positive population and an AUC of 1 to detect cervical cancer (FIG. 5B).

Thereby these genes provide promising triage markers in screening by primary HPV testing but can also be used as primary screening markers for both HPV and non-HPV related carcinomas.

Example 5: LHX8, ASCL1 and ST6GALNAC5 Methylation in Urine Specimens as Markers for Cervical Cancer and their High-Grade Precursor Lesions A total of 44 urine samples collected from patients with cervical cancer and 47 urine from control women were tested for LHX8, ASCL1 and ST6GALNAC5 methylation. Compared to controls LHX8, ASCL1 and ST6GALNAC5 methylation levels were significantly increased in urine samples of women with cervical cancer (FIG. 5A). Receiver Operating Characteristics analysis showed an AUC of 0,936 to detect cervical cancer (FIG. 5C). Importantly one cancer that was not detected by LHX8 or ASCL1 was detected by ST6GALNAC5, confirming the complementarity of the markers within the classifier. These results show that detection of the methylation classifier genes allows for cervical cancer screening using urine, thereby providing the most easy and most patient friendly non-invasive cancer screening methods currently available. Additionally methylation testing can be used to triage hrHPV-positive women in urine-based HPV screening programs.

Example 6: LHX8, ASCL1 and ST6GALNAC5 Methylation in Cervical Scrapes of Women with Endometrial Carcinoma A total of 24 cervical scrapes of women with endometrial carcinoma were tested for LHX8, ASCL1 and ST6GALNAC5 methylation. Compared to cervical scrapes of hrHPV negative and positive women in whom at maximum CIN 1 was diagnosed, LHX8, ASCL1 and ST6GALNAC5 methylation levels were significantly increased in women with endometrial carcinoma (FIG. 6).

TABLE 1

Primer and probe sequences (5'-3') used for LHX8, ASCL1 and ST6GALNAC5 quantitative MSP analysis

|  | Forward primer | Reverse primer | Probe |
| --- | --- | --- | --- |
| ASCL1 | CGTTTAAGTAAGTTAAGCGATAGCGTTC (SEQ ID NO: 1) | CCACGACGACCGACTACTACTACG (SEQ ID NO: 2) | GTTGTAAACGTCGGTTTAATTTTAGC (SEQ ID NO: 7) |

TABLE 1-continued

Primer and probe sequences (5'-3') used for LHX8, ASCL1 and ST6GALNAC5 quantitative MSP analysis

| | Forward primer | Reverse primer | Probe |
|---|---|---|---|
| LHX8 | TAGGCGTCGTGACGGT TGTAC (SEQ ID NO: 3) | AAACAAATCAAAAATTC CGAACG (SEQ ID NO: 4) | GTTTCGTATTTTGAGGGTT TTTATTAGTTCGTTTTTCG (SEQ ID NO: 8) |
| ST6GALNAC5 | GACGGTGTTTTTTTTG TTTTAGTTGC (SEQ ID NO: 5) | GCAACTAAAACAAAAAA AAC (SEQ ID NO: 6) | TGCGGCGGGGTTGGGGTTT A (SEQ ID NO: 9) |

Also Further Primers and Probes can be Useful in the Present Invention (Also in View of Examples 7-9), these are Listed in Table 2:

TABLE 2

Primer and probe sequences (5'-3') used for ZIC1, ASCL1, LHX8 and ZNF-582 quantitative MSP analysis

| | Forward primer | Reverse primer | Probe |
|---|---|---|---|
| ZIC1 | GGGCGGGTTAATGAGTTG C (SEQ ID NO: 10) | TCACGTACTACCGACGC TAACG (SEQ ID NO: 11) | CGCCGCGCCAACGAAAAAC (SEQ ID NO: 18) |
| ZNF-582 | TTTAAGGTCGGGTTGTTG TTTTTAC (SEQ ID NO: 12) | GCACAAAACACACCGAT ACTACG (SEQ ID NO: 13) | ATAATAAAACCGACGCCGCAAT ATCTTCCG (SEQ ID NO: 19) |
| LHX8 | CGTCGTGACGGTTGTAC (SEQ ID NO: 14) | CTCGACGCGAAAAACG (SEQ ID NO: 15) | TCAAAATACGAAACAACG (SEQ ID NO: 20) |
| ASCL1 | AGTAAGTTAAGCGATAGC GTTC (SEQ ID NO: 16) | ACCGCTAAAATTAAACC GACG (SEQ ID NO: 17) | TTCGTTCGAATTGATGCGTT (SEQ ID NO: 21) |

Example 7: LHX8, ASCL1, ST6GALNAC5, ZNF-582 and ZIC1 Methylation for the Detection of Vulvar Cancer and Precancer Vulvar intra-epithelial neoplasia (VIN) is the precursor lesion of vulvar squamous cell carcinoma (VSCC) but only a minority of VIN progresses to cancer. High-grade vulvar intraepithelial neoplasia (VIN) is the precancerous state of vulvar squamous cell carcinomas (VSCC), but only a minority of VINs progress to cancer, indicating a heterogeneous disease. Current clinical and histological classifications are insufficient to predict the cancer risk. Consequently, affected women are treated similarly with mutilating interventions. Hence, there is a clinical need for objective biomarkers reflecting the cancer risk. Therefore, we assessed the potential value of the DNA methylation marker panel LHX8, ASCL1 and ST6GALNAC5 as well as the methylation marker ZNF-582 and ZIC1 for risk stratification of VIN. The marker ZNF-582 was identified in the same genome-wide screen as described in Example 1. FIG. 7 shows the ZNF582 5'regulatory region and coding sequence (exon 1). The coding sequence is in upper case and underlined is the CpG rich region.

ZIC1 was identified in a previous genome-wide screen for detection of cervical precancer and cancer (Verlaat et al., Clinical Cancer Research, 2017). FIG. 8 shows the ZIC1 5'regulatory region and coding sequence (exon 1). The coding sequence is in upper case and the CpG rich regions are indicated in grey.

Eight normal vulva samples (controls), 39 VIN and 75 VSCC were included in this study. Of the 39 VIN, 25 were associated with VSCC (VIN with VSCC) and 14 not (VIN without VSCC, i.e. no development of VSCC during >10 years of follow-up. This unique series of well-characterized VIN lesions with clinical follow-up enables the identification of markers that distinguish VIN lesions with a high cancer risk in need of aggressive treatment from VIN lesions that have a low cancer risk and would benefit from a more conservative, e.g. non-invasive management.

Figure 9:
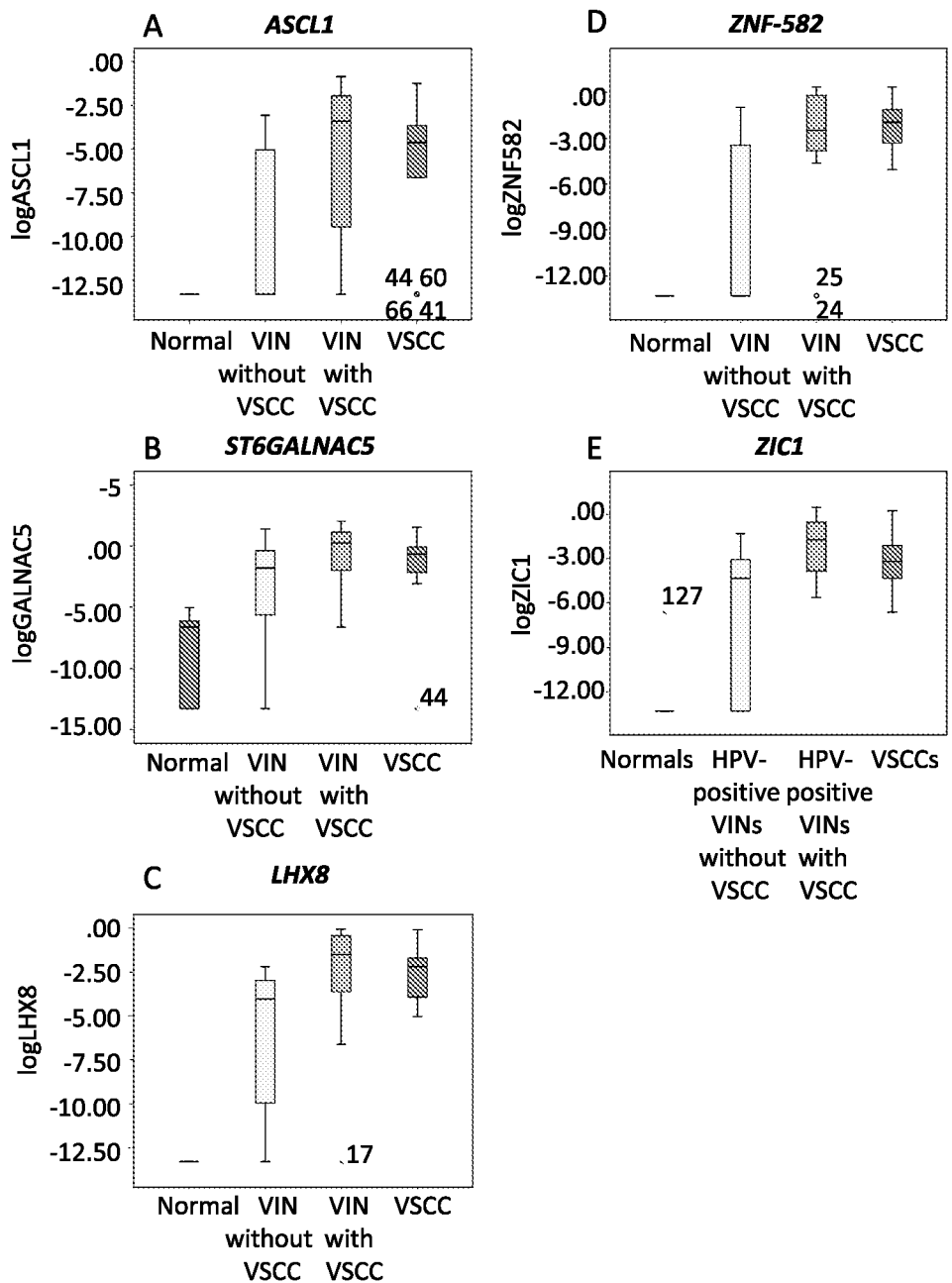
FIG. 9 shows the boxplots of the methylation levels of (A) ASCL1, (B) ST6GALNAC5, (C) LHX8, (D) ZNF-582 and (E) ZIC1 in vulvar tissue specimens. $\text{Log}_2$-transformed DNA methylation levels relative to reference gene ACTB (y-axis) are depicted for normal vulvar epithelium (green), VIN without (yellow) and with (orange) VSCC and VSCCs (red). DNA methylation levels are significantly increased in VIN at risk of cancer (VIN with VSCC; orange) and VSCC (red) compared to VIN without cancer (yellow) and normal vulvar epithelium (green). VIN: vulvar intraepithelial neoplasia; VSCC: vulvar squamous cell carcinoma.

Testing for LHX8, ASCL1, ST6GALNAC5 and ZNF-582 methylation showed differential methylation between HPV-positive VIN without VSCC and VIN with VSCC of all five genes (FIG. 9).

Receiver Operating Characteristic (ROC) curves for the comparison HPV-positive VIN without VSCC vs. HPV-positive VIN with VSCC based on logistic regression, yielded AUCs of 0.83 (LHX8), 0.80 (ASCL1), 0.69 (ST6GALNAC5), 0.80 (ZNF-582) and 0.78 (ZIC1).

Analysis of marker combinations revealed an increased AUC when combining two markers: ASCL1 plus ZIC1 (AUC=0.82), ASCL1 plus ZNF-582 (AUC=0.82) and ASCL1 plus LHX8 (AUC=0.83) These data indicate that a combination of two of the methylation markers LHX8, ASCL1, ZIC1 and ZNF-582 can be used for cancer risk stratification of HPV-positive VIN and for the detection of VSCC.

Example 8: Methylation Markers for the Detection of Anal Cancer and Precancer

Anal cancer is caused by high-risk HPV and preceded by precursor lesions: anal intraepithelial neoplasia (AIN;

graded 1-3). Since only a minority will eventually progress to cancer, preferably only lesions with high malignant potential are treated. Unfortunately, a predictive cancer progression marker is lacking. Currently all high-grade AIN is treated, resulting in significant overtreatment. Therefore, we assessed the potential value of DNA methylation markers ASCL1, ST6GALNAC5, ZIC1 and ZNF-582 for risk stratification of AIN. The markers ZIC1 and ZNF-582 were identified by genome-wide analysis in HPV-containing samples (see Example 1 and Verlaat et al., Clinical Cancer Research, 2017).

Figure 10:
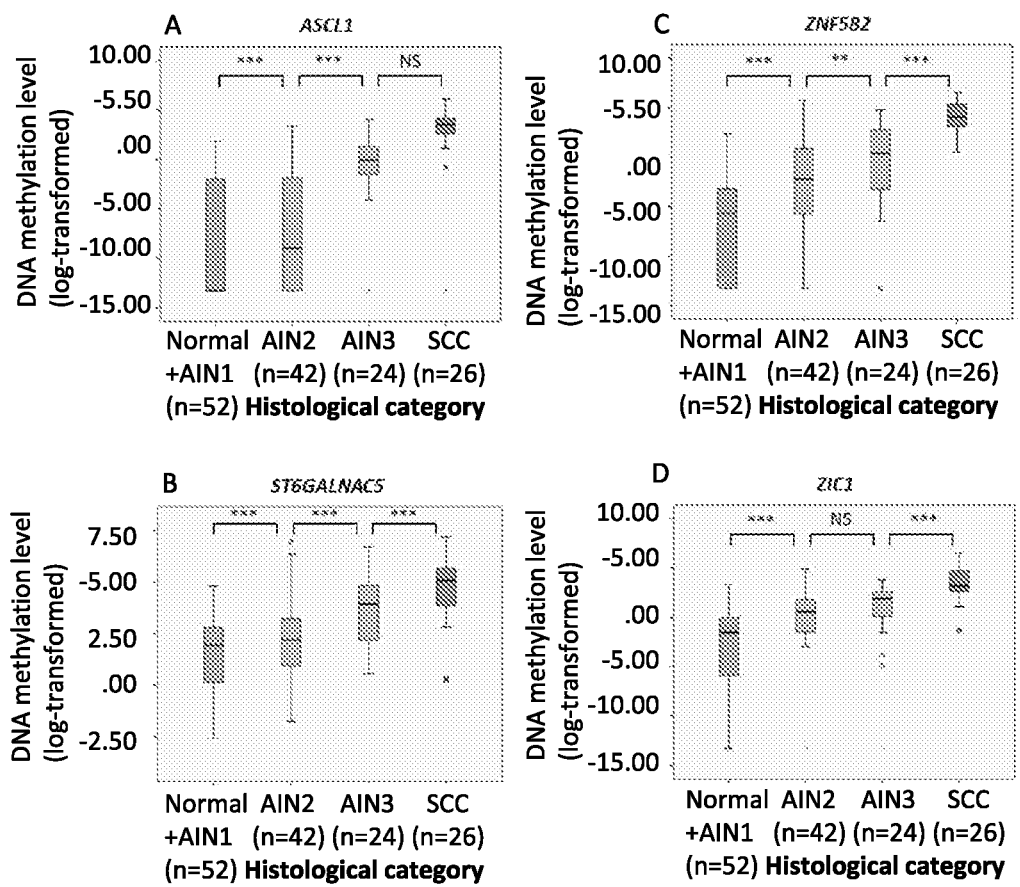
FIG. 10 shows the boxplots of the methylation levels of: (A) ASCL1, (B) ST6GALNAC5, (C) ZNF-582 and (D) ZIC1 in anal tissue specimens. $\text{Log}_2$-transformed DNA methylation levels relative to reference gene ACTB (y-axis) are depicted for the different histological categories of anal tissue specimens from HIV-positive men (X-axis). Normal and AIN1 (green), AIN2 and AIN3 (orange) and cancer (SCC; red) * and °: extreme and mild outlier samples, respectively. Methylation levels of all 4 marker increase significantly with severity of anal disease. : p<0.01, *: p<0.001, NS: not significant.

Archival tissue samples of HIV+ men with anal squamous cell carcinoma (SCC; n=26), AIN3 (n=24), AIN2 (n=42) and men without AIN2 or worse (normal+AIN1; n=56) were analysed for DNA methylation of four genes known to display hypermethylation during HPV-induced carcinogenesis using quantitative methylation-specific PCR. Methylation levels of all 4 genes were significantly higher with increasing severity of disease (FIG. 10). Logistic regression and AUC analysis was used to determine the performance of the methylation markers for the detection of anal cancer and AIN3. The AUCs for detecting AIN3 or worse were 0.89 (ASCL1), 0.84 (ST6GALNAC5), 0.87 (ZIC1) and 0.91 (ZNF-582).

Analysis of marker combinations revealed an even further improved detection of AIN3 or worse, with an AUC of 0.90 for ASCL1 plus ZIC1 and 0.92 for ASCL1 plus ZNF-582. Importantly, both marker combinations detected all anal cancers.

These data indicate that the methylation marker combinations ASCL1 plus ZIC1 and ASCL1 plus ZNF-582 can be used to detect anal cancer and high-grade AIN at risk of progression to cancer, which is particularly important for the clinical management of HIV-positive men having sex with men.

Example 9: LHX8, ASCL1, and ZIC1 Methylation in Cervical Scrapes of Women with Ovarian Cancer A total of 6 cervical scrapes of women with ovarian cancer, including both serous and clear cell cancers, were tested for LHX8, ASCL1 and ZIC1 methylation. Compared to cervical scrapes of women without disease (i.e. hrHPV negative and positive women in whom at maximum CIN 1 was diagnosed), LHX8, ASCL1 and ZIC1 methylation levels were significantly increased in women with ovarian cancer. These data indicate that a combination of any of these three markers enables the detection of ovarian cancer in cervical scrapes.

The invention claimed is:

1. A kit for detecting HPV-induced high-grade precancerous lesion or HPV-induced invasive carcinoma or nonHiPV-induced gynaecological or anogenital cancer, said kit comprising means for the specific amplification of a bisulfite modified sequence of ASCL1 and LHX8 and detection of ASCL1 and LHX8 methylation, wherein said means comprise:

(i) a probe and primers for methylation specific PCR, wherein said probe and primers are specific for a bisulfite modified sequence of the ASCL1 nucleotide sequence of SEQ ID NO: 22 and that target a CpG rich sequence in said bisulfite modified sequence, wherein said probe and/or primers comprise a detectable label, wherein said primers comprise a first primer consisting of the sequence of SEQ ID NO: 1 or the sequence of SEQ ID NO: 16 and a second primer consisting of the sequence of SEQ ID NO: 2 or the sequence of SEQ ID NO: 17; and (ii) a probe and primers for methylation specific PCR, wherein said probe and primers are specific for a bisulfite modified sequence of the LHX8 nucleotide sequence of SEQ ID NO: 23 and that target a CpG rich sequence in said bisulfite modified sequence, wherein said probe and/or primers comprise a detectable label.

2. The kit of claim 1 further comprising:
means for the detection of HPV infection, wherein said means comprise probes and primers specific for HPV.

3. The kit of claim 1, further comprising a brush or spatula to take a cervical scrape, an irrigation syringe, a disposable female urine catheter and/or a container to collect urine.

4. The kit of claim 3, comprising a brush or spatula to take a cervical scrape.

5. The kit of claim 1, wherein said primers specific for a bisulfite modified sequence of the LHX8 nucleotide sequence of SEQ ID NO: 23, comprise a first primer consisting of the sequence of SEQ ID NO: 3 or the sequence of SEQ ID NO: 14, and a second primer consisting of the sequence of SEQ ID NO: or the sequence of SEQ ID NO: 15.

6. The kit of claim 5, wherein said probe specific for a bisulfite modified sequence of the LHX8 nucleotide sequence of SEQ ID NO: 23 consists of the sequence of SEQ ID NO: 8 or the sequence of SEQ ID NO: 21.

7. The kit of claim 1, said kit further comprising means for the specific amplification and detection of ST6GALNAC5 methylation, wherein said means comprise:

a probe and primers for methylation specific PCR, wherein said probe and primers are specific for a bisulfite modified sequence of the ST6GALNAC5 nucleotide sequence of SEQ ID NO: 24 and that target a CpG rich sequence in said bisulfite modified sequence, wherein said probe and/or primers have a detectable label.

8. The kit of claim 7, further comprising:

means for the detection of HPV infection, wherein said means comprise probes and primers specific for HPV.

9. The kit of claim 7, further comprising a brush or spatula to take a cervical scrape, an irrigation syringe, a disposable female urine catheter and/or a container to collect urine.

10. The kit of claim 7, wherein said primers and probe specific for a bisulfite modified sequence of the ST6GALNAC5 nucleotide sequence of SEQ ID NO: 24 consist of the sequences of SEQ ID NO: 5, 6 and 9.

11. The kit of claim 1, said kit further comprising means for the specific amplification of a bisulfite modified sequence of at least one of ZIC1 and ZNF-582 and detection of at least one of ZIC1 and ZNF-582, wherein said means comprises one or more of:

a probe and primers for methylation specific PCR, wherein said probe and primers are specific for a bisulfite modified sequence of the ZNF-582 nucleotide sequence of SEQ ID NO:25 and that target a CpG rich sequence in said bisulfite modified sequence, wherein said probe and/or primers comprise a detectable label, a probe and primers for methylation specific PCR, wherein said probe and primers are specific for a bisulfite modified sequence of the ZIC1 nucleotide sequence of SEQ ID NO:26 and that target a CpG rich sequence in said bisulfite modified sequence, wherein said probe and/or primers comprise a detectable label.

12. The kit of claim 11, further comprising:

means for the detection of HPV infection, wherein said means comprise probes and primers specific for HPV.

13. The kit of claim 11, further comprising a brush or spatula to take a cervical scrape, an irrigation syringe, a disposable female urine catheter and/or a container to collect urine.

14. The kit of claim 11, wherein said primers and probe specific for a bisulfite modified sequence of the ZIC1 nucleotide sequence of SEQ ID NO: 26 consist of the sequences of SEQ ID NO: 10, 11 and 18 or said primers and probe specific for a bisulfite modified sequence of the ZNF-582 nucleotide sequence of SEQ ID NO: 25 consist of the sequences of SEQ ID NO: 12, 13 and 19, or said primers and probe specific for a bisulfite modified sequence of the ZIC1 nucleotide sequence of SEQ ID NO: 26 consist of the sequences of SEQ ID NO: 10, 11 and 18 and said primers and probe specific for a bisulfite modified sequence of the ZNF-582 nucleotide sequence of SEQ ID NO: 25 consist of the sequences of SEQ ID NO: 12, 13 and 19.

15. The kit of claim 1, comprising at least one probe or primer having a modified nucleotide.

16. The kit of claim 1, wherein said probe specific for a bisulfite modified sequence of the ASCL1 nucleotide sequence of SEQ ID NO: 22 consists of the sequence of SEQ ID NO: 7 or the sequence of SEQ ID NO: 20.

* * * * *

UNITED STATES PATENT AND TRADEMARK OFFICE
CERTIFICATE OF CORRECTION

| | |
|---|---|
| PATENT NO. | : 11,932,909 B2 |
| APPLICATION NO. | : 16/491182 |
| DATED | : March 19, 2024 |
| INVENTOR(S) | : Christophorus Joannes Lambertus Maria Meijer et al. |

It is certified that error appears in the above-identified patent and that said Letters Patent is hereby corrected as shown below:

In the Claims

Column 37, Line 53, change nonHiPV to -- nonHPV --.

Signed and Sealed this
Twenty-ninth Day of October, 2024

Katherine Kelly Vidal
*Director of the United States Patent and Trademark Office*

SEQUENCE LISTING

```
<160> NUMBER OF SEQ ID NOS: 26

<210> SEQ ID NO 1
<211> LENGTH: 28
<212> TYPE: DNA
<213> ORGANISM: Artificial Sequence
<220> FEATURE:
<223> OTHER INFORMATION: primer

<400> SEQUENCE: 1
cgtttaagta agttaagcga tagcgttc                                       28

<210> SEQ ID NO 2
<211> LENGTH: 24
<212> TYPE: DNA
<213> ORGANISM: Artificial Sequence
<220> FEATURE:
<223> OTHER INFORMATION: primer

<400> SEQUENCE: 2
ccacgacgac cgactactac tacg                                           24

<210> SEQ ID NO 3
<211> LENGTH: 21
<212> TYPE: DNA
<213> ORGANISM: Artificial Sequence
<220> FEATURE:
<223> OTHER INFORMATION: primer

<400> SEQUENCE: 3
taggcgtcgt gacggttgta c                                              21

<210> SEQ ID NO 4
<211> LENGTH: 23
<212> TYPE: DNA
<213> ORGANISM: Artificial Sequence
<220> FEATURE:
<223> OTHER INFORMATION: primer

<400> SEQUENCE: 4
```

```
aaacaaatca aaaattccga acg                                                    23
```

<210> SEQ ID NO 5
<211> LENGTH: 26
<212> TYPE: DNA
<213> ORGANISM: Artificial Sequence
<220> FEATURE:
<223> OTHER INFORMATION: primer

<400> SEQUENCE: 5

```
gacggtgttt tttttgtttt agttgc                                                 26
```

<210> SEQ ID NO 6
<211> LENGTH: 20
<212> TYPE: DNA
<213> ORGANISM: Artificial Sequence
<220> FEATURE:
<223> OTHER INFORMATION: primer

<400> SEQUENCE: 6

```
gcaactaaaa caaaaaaaac                                                        20
```

<210> SEQ ID NO 7
<211> LENGTH: 26
<212> TYPE: DNA
<213> ORGANISM: Artificial Sequence
<220> FEATURE:
<223> OTHER INFORMATION: probe

<400> SEQUENCE: 7

```
gttgtaaacg tcggtttaat tttagc                                                 26
```

<210> SEQ ID NO 8
<211> LENGTH: 38
<212> TYPE: DNA
<213> ORGANISM: Artificial Sequence
<220> FEATURE:
<223> OTHER INFORMATION: probe

<400> SEQUENCE: 8

```
gtttcgtatt ttgagggttt ttattagttc gttttcg                                     38
```

<210> SEQ ID NO 9
<211> LENGTH: 20
<212> TYPE: DNA
<213> ORGANISM: Artificial Sequence
<220> FEATURE:
<223> OTHER INFORMATION: probe

<400> SEQUENCE: 9

```
tgcggcgggg ttgggttta                                                         20
```

<210> SEQ ID NO 10
<211> LENGTH: 19
<212> TYPE: DNA
<213> ORGANISM: Artificial Sequence
<220> FEATURE:
<223> OTHER INFORMATION: primer

<400> SEQUENCE: 10

```
gggcgggtta atgagttgc                                                         19
```

<210> SEQ ID NO 11
<211> LENGTH: 22
<212> TYPE: DNA

```
<213> ORGANISM: Artificial Sequence
<220> FEATURE:
<223> OTHER INFORMATION: primer

<400> SEQUENCE: 11
tcacgtacta ccgacgctaa cg                                              22

<210> SEQ ID NO 12
<211> LENGTH: 25
<212> TYPE: DNA
<213> ORGANISM: Artificial Sequence
<220> FEATURE:
<223> OTHER INFORMATION: primer

<400> SEQUENCE: 12
tttaaggtcg ggttgttgtt tttac                                           25

<210> SEQ ID NO 13
<211> LENGTH: 23
<212> TYPE: DNA
<213> ORGANISM: Artificial Sequence
<220> FEATURE:
<223> OTHER INFORMATION: primer

<400> SEQUENCE: 13
gcacaaaaca caccgatact acg                                             23

<210> SEQ ID NO 14
<211> LENGTH: 17
<212> TYPE: DNA
<213> ORGANISM: Artificial Sequence
<220> FEATURE:
<223> OTHER INFORMATION: primer

<400> SEQUENCE: 14
cgtcgtgacg gttgtac                                                    17

<210> SEQ ID NO 15
<211> LENGTH: 16
<212> TYPE: DNA
<213> ORGANISM: Artificial Sequence
<220> FEATURE:
<223> OTHER INFORMATION: primer

<400> SEQUENCE: 15
ctcgacgcga aaaacg                                                     16

<210> SEQ ID NO 16
<211> LENGTH: 22
<212> TYPE: DNA
<213> ORGANISM: Artificial Sequence
<220> FEATURE:
<223> OTHER INFORMATION: primer

<400> SEQUENCE: 16
agtaagttaa gcgatagcgt tc                                              22

<210> SEQ ID NO 17
<211> LENGTH: 21
<212> TYPE: DNA
<213> ORGANISM: Artificial Sequence
<220> FEATURE:
<223> OTHER INFORMATION: primer

<400> SEQUENCE: 17
accgctaaaa ttaaaccgac g                                               21
```

```
<210> SEQ ID NO 18
<211> LENGTH: 19
<212> TYPE: DNA
<213> ORGANISM: Artificial Sequence
<220> FEATURE:
<223> OTHER INFORMATION: probe

<400> SEQUENCE: 18
cgccgcgcca acgaaaaac                                                    19

<210> SEQ ID NO 19
<211> LENGTH: 30
<212> TYPE: DNA
<213> ORGANISM: Artificial Sequence
<220> FEATURE:
<223> OTHER INFORMATION: probe

<400> SEQUENCE: 19
ataataaaac cgacgccgca atatcttccg                                        30

<210> SEQ ID NO 20
<211> LENGTH: 18
<212> TYPE: DNA
<213> ORGANISM: Artificial Sequence
<220> FEATURE:
<223> OTHER INFORMATION: probe

<400> SEQUENCE: 20
tcaaaatacg aaacaacg                                                     18

<210> SEQ ID NO 21
<211> LENGTH: 20
<212> TYPE: DNA
<213> ORGANISM: Artificial Sequence
<220> FEATURE:
<223> OTHER INFORMATION: probe

<400> SEQUENCE: 21
ttcgttcgaa ttgatgcgtt                                                   20

<210> SEQ ID NO 22
<211> LENGTH: 2329
<212> TYPE: DNA
<213> ORGANISM: Homo sapiens

<400> SEQUENCE: 22
ttctttatga tatccgctaa gctggtccgg aaataatctt tatggggagg gggtggcggt        60 aggggcgat ggtacagggg gccagaggtc atcctagggg gacgtccctg ccatatacac        120
ccacctacag gacggctcac aaccactcct cggtgtcgct tccccgcggc cccccacaca       180
cttgctcagt tatggggagc acatcctagt ttttagagct gaatgggaca ttagagacca       240
tattctgtgg ctgcagacga ggaagcgaag gctcagagag gatgccactt cgaggagcca       300
cagagcattg agaggacgcc ttgggactag aacccacgtt ttcacatagt ccagcacttt       360
ttttcactgt tctggacgga gtccctcccc caaccatgtt tctaaacttc aatcgtaatt       420
tgctccaatt tctagggtca ccgaggaacc cgaagagaat aacagtgagg agagagagaa       480
aacaggaaaa gtcgagcccc actccctcct cacctccaca ccgttcctgt gccattttt        540 ctgcccaaac ccttccctgc gctttgcttc aagttcttag tagaatccaa gagagcttca       600
ccccaagtct ttccacctat acacctcaat tcctagagcc atttgtccct cctgtgacgc       660
```

```
cccccacccc cttcctaaag ccaccccgg  cagcagcccg ccccgagcgc gccgcctgtt     720
tattcagccg ggagtccggc acgcgccagg cgcacgcact gcaacaacaa acccagctga     780
atggagagtt tgcaaggagc gggagaaagg aacgggaggg ggggagagga gaggaggagg     840
gggagtttag ggagtggggtg ggaggaagag gtaagaggag ggggggggagt ggggggctgca   900 gccgctcgct gcagcagcgg ggagtggggg gcgaggcggg gccagggctg cgcgtggggc     960
tgggtgtccc attgaaaagg cggacgcact ccggcagccc agcactctct cacttctggc    1020
cagggaacgt ggaaggcgca ccgacaggga tccggccagg gagggcgagt gaaagaagga    1080
aatcagaaag gaagggagtt aacaaaataa taaaaacagc ctgagccacg gctggagaga    1140
ccgagacccg gcgcaagaga gcgcagcctt agtaggagag gaacgcgaga gcggcagag    1200 gcgttcagc actgactttt gctgctgctt ctgcttttt ttttcttaga aacaagaagg     1260
cgccagcggc agcctcacac gcgagcgcca ccgcgaggct ccgaagccaa cccgcgaagg    1320
gaggagggga gggaggagga ggcggcgtgc agggaggaga aaaagcattt tcactttttt    1380
tgctcccact ctaagaagtc tcccggggat tttgtatata ttttttaact tccgtcaggg    1440
ctcccgcttc atatttcctt ttctttccct ctctgttcct gcacccaagt tctctctgtg    1500
tccccctcgc gggccccgca cctcgcgtcc cggatcgctc tgattccgcg actccttggc    1560
cgccgctgcg catggaaagc tctgccaaga tggagagcgg cggcgccggc cagcagcccc    1620
agccgcagcc ccagcagccc ttcctgccgc ccgcagcctg tttctttgcc acggccgcag    1680
ccgcggcggc cgcagccgcc gcagcggcag cgcagagcgc gcagcagcag cagcagcagc    1740
agcagcagca gcagcaggcg ccgcagctga gaccggcggc cgacgccag ccctcagggg    1800 gcggtcacaa gtcagcgccc aagcaagtca gcgacagcg ctcgtcttcg cccgaactga    1860
tgcgctgcaa acgccggctc aacttcagcg gctttggcta cagcctgccg cagcagcagc    1920
cggccgccgt ggcgcgccgc aacgagcgcg agcgcaaccg cgtcaagttg gtcaacctgg    1980
gctttgccac ccttcgggag cacgtcccca acggcgcggc caacaagaag atgagtaagg    2040
tggagacact gcgctcggcg gtcgagtaca tccgcgcgct gcagcagctg ctggacgagc    2100
atgacgcggt gagcgccgcc ttccaggcag gcgtcctgtc gcccaccatc tccccccaact    2160 actccaacga cttgaactcc atggccggct cgccggtctc atcctactcg tcggacgagg    2220
gctcttacga cccgctcagc cccgaggagc aggagcttct cgacttcacc aactggttct    2280
gaggggctcg gcctggtcag gccctggtgc gaatggactt tggaagcag                2329
```

<210> SEQ ID NO 23
<211> LENGTH: 2456
<212> TYPE: DNA
<213> ORGANISM: Homo sapiens

<400> SEQUENCE: 23

```
acatgtagaa gggcgggttt tcctgaaaga ggcgaagcaa tttctccagg aaagactttc      60
ccccacacga ccccttcct ttatattagg ttccaccctc tggaaaacaa aactttttt     120 tttttctttt cctggaggga ctcaggaaaa gctcagtgct cacttcactc agagctcagt     180
gaagctggga aaggaatttt aagaacggtt catcagaaag tggtcaggcc acagcggcct    240
ctttggacga agacacactt gtagcattat ccttctcggc atcagctttt attagtggat    300
cggggcgggg gagggggag atcggcagac acgacagcc tctgaccctc tggagttggt     360
atgtgataag cagccctagc agtgccatgt attggaagaa cgatcagatg tttgtgtgta    420
aactagtagc aaaggacgtg ccggagctgg cagttccccc tgagaaggtg agcgagccga    480
```

```
cgcctggcca gaccagctga atcgcagtgt ccttgaaact cgagttgttt gggctcctaa      540
acaaggttca gaaactacct gtaacggcct catcttcaga cctggcaatt tttttttttt      600
attacgtagt agcgttagtc agtaatcatt gcactccctc cccaaaagct cacttaacct      660
gagacatgga gactgtaatt tgggagatga agcctcgagc ctaaggcgct ctcaggtcca      720
tgtgagtcgt gcttttgttc tatttgctgt ggtgatcgtg gcggtccggg agagtgggtc      780
gggaggactg ggcggctgtc gggtggaacc ggagacctgg ctcgtttcgt tcggctgccc      840
gcggacactt gcctgccctg aggcacacct ccctctgcgg ggctccagaa aggcctccgg      900
gatccctggg cttgccggga gagccatttt acctaaaatg ccaaaagaaa accgcagggc      960
acaaaacgag tcacgcggtt tgtctgagta gactggggaa gctgacaagc tctcacctca     1020
ctcgggaggc aggacctgtg ggtatttggt gttttaagtt tgaaatcatc tgcagcctgt     1080
ctgagggcct cagcaggacg cgcgcggggc gccctgact atttctttgc tccgaagccg     1140 gttgggggaca ccaggcgaaa gcggagctgt tctgttttaaa cgccctttgt gtgtgaggac     1200
gcggcctcag tgcagctacg ctgggtcccg cgtagggagc gcaccccaga aagggagggt     1260
ctcggccgac ggtccgggag gcccccaggt tggtatcttg cctggtgctt ccagagggag     1320
ggagaagggg aggcgaacag tcagaaatgc agaagtgcga gccgctcgag ttcggggtac     1380
ccacccgccc ccgagctaga gtttttggaa acgaaagcgg tctaagccca gggacgctgc     1440
gttttcgttt aagaacaaaa ctccagcaaa tacttggaaa cacttgagta acgcgcgttg     1500
tttctttaaa acattttgtc agaggttggg tgagttcttt taatggcaca aattaaattc     1560
agctggatat tttccattat tctacccgct tttttgcgctg gttaaaaata atcctttagt     1620
agctcaaatg ttgacttact gagcaataag tggcaattta cccttaaag aaacgagtgt     1680 aaatcactcg ccactctaat tgctgtaagt ttacgaaaga gctgctggct cggtttaatc     1740
tgaagcattt tcattcaaat tgtcatcgga acaaacacca ggcttcttaa atcccgctgt     1800
aattagcttt caagtatcct attaaacctc ttcacctttc gggctatcct attcaaaaag     1860 ccccctttt aaaatatata tgtgtcttgc tcttttaatt gaggttatta agaaatcta     1920 gtttcttctc ccacccctc ctcaatcctc ttttcttctc tcgcactcca cctcccactg     1980
ccccgcaccc cctttagccc ggtgttcccc gctccgctat gattgacgtc tggaaagaaa     2040
gagctttgtg aggggatgat tgttattaac ttgttatccc cggcggggg gcggggaacc     2100 gacgtgcccg ggtgagcgcc ggagacccgg agcccgggga gcgcgggacg agctaccagc     2160
gctcgggtgg cggccgccag cggccagcga aggaggctgc cgccagccc gcccgcggcg     2220 cccgggctca ggcgccgtga cggctgcacg cgctgccccg cactctgagg gccttcatta     2280
gctcgctccc cgcgccgagg ctgggcgggg cagcacgctc ggaacttctg atctgtttct     2340
ccatactttc tccccctcct actccgcagt gtcagggct catgtcagag gagtgcgggc     2400
ggactacagc cctggcggcc gggaggactc gcaaaggcgc cggggaagag ggactg        2456
```

<210> SEQ ID NO 24
<211> LENGTH: 2242
<212> TYPE: DNA
<213> ORGANISM: Homo sapiens

<400> SEQUENCE: 24

```
agatgttaag taatacatta agacaactat tttcactgag caatttcaca agaaatatgt       60
ttttagctaa attagacatt taacaaatgc catttgtaat tcaatgcaga ggagacagca      120
```

| | |
|---|---|
| tccttaaaac aagctattga tgtgactttc caacataaa acaatactta tgttttttta | 180 |
| attttaattg aagtcctgaa tgtgaaacta tcgccgtcag tgcagtagac caacggaaag | 240 |
| caccaaatac cttaggatta tgaaataagc catatgcagt tttatctcta gcagacagaa | 300 |
| attcttcatc caaattagga agaatctaca ggtcaagtta atcatgtagc tgtgacgtgc | 360 |
| tgaatgtttt taaaacttta agatcattta gatgaacact aggaaactca gaggtcaggc | 420 |
| agaaatgtaa attgtaatat tcaatgaaaa taataaatga aataattgag atgaaatatt | 480 |
| atctaaagaa tgcatgagaa taactgaatc tgataaagta aaattaaaat taagagagaa | 540 |
| gagaaaataa gaaagtgagc aattgaaaaa cggaataata aataattttt taagaaaaat | 600 |
| aatttcatca tgtatttctc tatgctacgt acataaacgc aaacgctata aatagagtta | 660 |
| ttgacatttg ggaggttgat tgttttttat caacatcgca aaacagaaaa tttaggttgc | 720 |
| agattttcac atggctatca cgttcagaat ccaatcaggt tctccttctt tactacttga | 780 |
| tgacttcttt aaagataaat aagcccgcgg accaagaagt gggtacactg gctcggttaa | 840 |
| ctctctctcc ccagaaattt cactactgaa agattatta tttgggggcg gggaagggaa | 900 |
| tgtagaggtc tttaggaccc agcaggcggc ggcaggcggc agttgtgtag atcgctgaga | 960 |
| gactacgagg gtccggttca gttttaattc tgtctctaat ctctgcaaca gccgcgcttc | 1020 |
| ccgggtcccg cggctcccgc gcgcgatctg ccgcggccgg ctgctgggca aaaatcagag | 1080 |
| ccgcctccgc cccattaccc atcatggaaa ccctccagga aaaagtggcc ccggacgcgc | 1140 |
| gagcctgagg attctgcaca aaagaggtgc ccaaaatgaa gaccctgatg gtgagtcagt | 1200 |
| tgtggcaact ccaccgggca agagggggga tccccgggct cagggtccac gggacgcacc | 1260 |
| gtggagactc cgagacgcct aaccctgggc cgcgaggtcg cctgttacaa agggacaact | 1320 |
| ttctacccgc tccgcgttcc ctcccgattc tccagctctg cctggctcgg aatcccagag | 1380 |
| ccaggatggg aactcggggt tgcctcgcct cctagatctc cggcgagagg tccgaggggg | 1440 |
| tggcggagag ctgcaggagc gatggaggag tgggcagatt gctcaaggga tggggtgcc | 1500 |
| caaaagcaac agcctgccaa aaactaagag ggacggggag gggggacctt tgcagacttt | 1560 |
| cttcgttttc ttagatttca aacttgcaag gatcgcaagg atccaggagcc ccaggaaagg | 1620 |
| aggggtgtga aggactcaaa attccagcag cttggctggg gtggctgcgc cagacgggcc | 1680 |
| cttccccaaa gtgcaaaccc accctgtcc tcggccccgg cgcgctccct ccctcagccc | 1740 |
| ggggccgtac accacctgcc ctctaccgag agatctgggc ggcggcggcc gaaagcagcg | 1800 |
| acgcgcccgg agcatcccctt gcgatacgct aggggacggt gctttctctg tcccagttgc | 1860 |
| gtgcggcggg gctggggccc aggccgcccc aaatctcccc cactagagtg accaccgcac | 1920 |
| agttgtcccc gctgggcgcg ctcctccggt gtctgcgctc agccgctctc ctcttctctc | 1980 |
| tcccgcccgc ccgcagcgcc atggtctggc agtgtgttta gcgctcacca ccatgtgcac | 2040 |
| cagcttgttg ctagtgtaca gcagcctcgg cggccagaag gagcggcccc cgcagcagca | 2100 |
| gcagcagcag cagcaacagc agcagcaggc gtcggccacc ggcagctcgc agccggcggc | 2160 |
| ggagagcagc acccagcagc gccccggggt ccccgcggga ccgcggccac tggacggata | 2220 |
| cctcggagtg gcggaccaca ag | 2242 |

<210> SEQ ID NO 25
<211> LENGTH: 1026
<212> TYPE: DNA
<213> ORGANISM: Homo sapiens

<400> SEQUENCE: 25

-continued

```
agttcaggca ttctggctcc agtcttagag atggttaagg gttcacactc ttaaccattt    60
attacaccat agagctcacc aggtttgagg gaaacaggat caaatcaaaa gagtcactca   120
ggactccagt cctcactcaa ggacaaactg ttccacctcg gacagggaga gttccgcatt   180
ctgagaccca gcataacagg tcctgaccgg catctggcac tcggactccc aatcatactg   240
gatcacactg gctcgggatg tgtaaagtcc agggcttctc acatttgatg acaccaaatc   300
cgcctaaaaa caagagagaa ttaacaacta cctacggcgg tctgatattt gccaagagat   360
gccgccccat aaaactcctt tacatcttta taacgttttt attttgcgtt ctccttcata   420
acccacattt aactcaccat agatgtaatg tttaaaatta gttaccagat aaactcttac   480
gcttccaaac tttaaggttc cttcgaaacc ttctggtaaa actgttgttc cacggaaatg   540
ggaacgtaac ggatgaggca atcttccaca gccgcacaca gttgtgtatc caccgctaaa   600
cggtcccagt catacattca acgacccacg cggagtcaga agctaccacc acacactgtc   660
aaaatcacgc acacacagtg acggcccctt gcccactcgg tcactcgccc acaatctctc   720
gctagagaat cacacgcaga tagcacaccc agcaccacag accccaggaa gcaacccagg   780
gctcgaacac acgaacagca ctcctccgcg cactgcgcag gcacgcctgc gtccggctca   840
ccctgaaact atgtttcccg gaagacactg aggagaagga aatatcatgg cgcagcatcg   900
gtgtgctttg tgcgtctgcg ccatcttccg gctgcgcacg gcgaatccac cggtaccgtg   960
gtggaagcgc gccctgggct gccggggggcg cggccgcggt ggcacttgga cccgaggagg  1020
cggcag                                                             1026
```

<210> SEQ ID NO 26
<211> LENGTH: 2748
<212> TYPE: DNA
<213> ORGANISM: Homo sapiens

<400> SEQUENCE: 26

```
gagagacagg gttagcgggg gcagtcgaag gagacaacgg aaaggcagaa aacagaaaaa    60
taacgcaaga gagagaaaaa gtaaaggaaa ctggcaacaa cgtttcaaat ttgccattaa   120
aaaatcaaac ctcaataacc tgggaactta agcgctttca tccacctgtg tgtgtgagtg   180
tgtgtgtgtg tgtgttttcg gggagggggg tgcggtggtg ccggaagtct gattagataa   240
aagcgagaaa tacagaggct gccggttaca ctgagaaatt acatttttt gtaaagagag   300
catagtgccc gtgtgctccc aagatcttaa attataaaca ggaggggggac aaagcaagag   360
ggaaacaaac ttcaaaagga gcaaataaca aaagcctctt ttgctgctct tgaagggagg   420
ggggaagggg gaagaaagaa aagaaagttg ctgaatcggg acattctgga agtgcctttg   480
ctgtgtttac tagccccatc cccgcctgct gcacccggag acgtctgaag tctctaatcg   540
ctcagcgaaa agttggtttc gggaagggca gcgccggggt gcgggagggc aaaggaggaa   600
gaggaatgca tatgactgtg agaaggaaaa gtaatcgtgg caaaaaaaaa aaaaaaaaaa   660
aaaagaaag aaagaaaaga aaaagaaaa aaatttccg tgagaagagg gaaaaatttt   720
ggctaaaaaa aaagttgcta ctcctggcag ccctggtttg tcaaaagggg atgtcaagcg   780
ctttacaata cctgggattg atgaggcggg cgggccaatg agctgcgcgc ggcgcctcgg   840
cgcgccctcc gttggcgcgg cggctgaggg cgggggggaat gcgggcgcac caatgggcgc   900
cagcgtcggc agcacgtgac acctcccccc tgctcccatt catcaagggg gggacggtgt   960
cgtcctttca attcatttat ctgcaggaat gattgctgct atcagtctcg cgctcaccgc  1020
```

```
ccggctgagg aggtgaaagt ttctccccag gaagataaac cgcaaaagac aatattgtgc    1080
atgatttgcg cctttctttt ggctttttct ttctttcttc accccccccac ccactttttt    1140 ttttttttt ttcaaaaagc agagagggaa aaacggagag tgaaggagcg aggaggcgag    1200
cgtgagagaa aggagagaga gagaaaagaa agggcgaggg gctagtggag aagtaaggag    1260
gggcgcgctg cgcgaggcgg agagagggcg aagcagtcgc ggcactggcg ctcacattcc    1320
tctatgctac aaatccagga ggaagttttt ttttaggggg ctgagatgct ccatgccttt    1380
ccccgggcag ccttgacgcg cggccctctc ggcagagact gagcggcgag aaagtgcgag    1440 ccggccggc agaatctgcc tggcgggcgc tggagcctgc gttactcgcg gcccgcagcc    1500
gtccggctac tttgcgtttg gcccggccag cgcccgggcg cgccgcgcca ttgcctgcag    1560
gctaggactt cgcgaggtgg gtcgactccc cctccctcct cctcttcttc ctcctcttcc    1620
tcctcctctt gttcctcctc ctcctcccga ttttccctcc tcggctggcg agggtggggg    1680
gggcggggga ggccggggct cgccccgagc agccacgatg ctcctggacg ccggccccca    1740
gtacccagcg atcggcgtga ccacctttgg cgcgtcccgc caccactccg cgggcgacgt    1800
ggccgaacga gacgtgggcc tgggcatcaa cccgttcgcc gacggcatgg gcgccttcaa    1860
gctcaacccc agttcgcacg agctggcttc ggccggccag acggccttca cgtcgcaggc    1920
gccaggctac gcggctgctg cggccctggg ccatcaccat cacccgggcc acgtcggctc    1980
ctattccagc gcagccttca actccacgcg ggactttctg ttccgcaacc ggggttttgg    2040
cgacgcggcg gcggcagcca gcgcacagca cagcctcttt gctgcatcgg ccgggggctt    2100
cgggggccca cacggccaca cggacgccgc gggccacctc ctcttccccg ggcttcacga    2160
gcaggctgcc ggccacgcgt cgcctaacgt ggtcaacggg cagatgaggc tcggcttctc    2220
gggggacatg tacccgcgac cggagcagta cggccaggtg accagcccgc gttcggagca    2280
ctatgctgcg ccgcagctgc acggctacgg gcccatgaac gtgaacatgg ccgcgcatca    2340
cggcgccggc gccttcttcc gctacatgcg ccaacccatc aagcaagagc tcatctgcaa    2400
gtggatcgag cccgagcagc tggccaaccc caaaaagtcg tgcaacaaaa ctttcagcac    2460
catgcacgag ctagttacgc acgtcaccgt ggagcacgta ggtggcccgg agcagagtaa    2520
tcacatctgc ttctgggagg agtgtccgcg cgagggcaag cccttcaaag ccaaatacaa    2580
actggttaac cacatccgcg tgcacacggg cgagaagccc tttcccctgcc ccttccctgg    2640 ctgtggcaag gtcttcgcgc gctccgagaa tttaaagatc cacaaaagga cgcacacagg    2700
ggagaagccc ttcaagtgcg agtttgaggg ctgtgaccgg cgcttcgc                 2748
```